United States Patent
Coskun et al.

(10) Patent No.: US 8,557,769 B2
(45) Date of Patent: Oct. 15, 2013

(54) CO-ADMINISTRATION OF FGF-21 AND GLP-1 TO TREAT DIABETES AND LOWER BLOOD GLUCOSE

(75) Inventors: Tamer Coskun, Indianapolis, IN (US); Wolfgang Glaesner, San Diego, CA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/534,322

(22) Filed: Jun. 27, 2012

(65) Prior Publication Data

US 2012/0264683 A1 Oct. 18, 2012

Related U.S. Application Data

(63) Continuation of application No. 12/668,475, filed as application No. PCT/US2008/071508 on Jul. 30, 2008, now abandoned.

(60) Provisional application No. 60/953,785, filed on Aug. 3, 2007.

(51) Int. Cl.
*A61K 38/18* (2006.01)
*A61K 38/26* (2006.01)

(52) U.S. Cl.
USPC ............................................ 514/9.1; 514/7.2

(58) Field of Classification Search
None
See application file for complete search history.

(56) References Cited

U.S. PATENT DOCUMENTS

| | | |
|---|---|---|
| 6,191,102 B1 | 2/2001 | DiMarchi et al. |
| 7,084,243 B2 | 8/2006 | Glaesner et al. |
| 7,101,843 B2 | 9/2006 | Glaesner et al. |
| 7,271,149 B2 | 9/2007 | Glaesner et al. |
| 7,452,966 B2 | 11/2008 | Glaesner et al. |
| 7,482,321 B2 | 1/2009 | Glaesner et al. |
| 7,491,697 B2 | 2/2009 | Beals et al. |
| 7,576,190 B2 | 8/2009 | Glaesner et al. |
| 7,582,607 B2 | 9/2009 | Frye et al. |
| 7,622,445 B2 | 11/2009 | Frye et al. |

FOREIGN PATENT DOCUMENTS

| | | |
|---|---|---|
| WO | 98/19698 | 5/1998 |
| WO | 01/98331 | 12/2001 |
| WO | 02/46227 | 6/2002 |
| WO | 03/011213 | 2/2003 |
| WO | 03/018516 | 3/2003 |
| WO | 03/058203 | 7/2003 |
| WO | 2005/000892 | 1/2005 |
| WO | 2005/061712 | 7/2005 |
| WO | 2005/113606 | 12/2005 |
| WO | 2006/028595 | 3/2006 |
| WO | 2006/028714 | 3/2006 |
| WO | 2008/121563 | 10/2008 |

OTHER PUBLICATIONS

Edwards, et al., Exendin-4 reduces fasting and postprandial glucose and decreases energy intake in healthy volunteers, American Journal of Physiology: Endocrinology and Metabolism, American Physiological Society, 2001, E155-E161, 281.

*Primary Examiner* — Christine J Saoud
(74) *Attorney, Agent, or Firm* — Gregory A. Cox; Andrea M. Castetter

(57) ABSTRACT

The present invention provides methods of lowering body weight by administering an FGF-21 compound in combination with a GLP-1 compound. In addition, the present invention also provides methods to treat obesity by administering an FGF-21 compound in combination with a GLP-1 compound. The present invention also discloses combinations useful in the methods of the present invention.

2 Claims, No Drawings

SEQUENCE LISTING

```
<160> NUMBER OF SEQ ID NOS: 57

<210> SEQ ID NO 1
<211> LENGTH: 624
<212> TYPE: DNA
<213> ORGANISM: Homo sapiens

<400> SEQUENCE: 1
atggactcgg acgagaccgg gttcgagcac tcaggactgt gggtttctgt gctggctggt      60
ctgctgggag cctgccaggc acaccccatc cctgactcca gtcctctcct gcaattcggg     120
ggccaagtcc ggcagcggta cctctacaca gatgatgccc agcagacaga agcccacctg     180
gagatcaggg aggatgggac ggtggggggc gctgctgacc agagccccga aagtctcctg     240
cagctgaaag ccttgaagcc gggagttatt caaatcttgg gagtcaagac atccaggttc     300
ctgtgccagc ggccagatgg ggccctgtat ggatcgctcc actttgaccc tgaggcctgc     360
```

-continued

```
agcttccggg agctgcttct tgaggacgga tacaatgttt accagtccga agcccacggc    420
ctcccgctgc acctgccagg gaacaagtcc ccacaccggg accctgcacc ccgaggacca    480
gctcgcttcc tgccactacc aggcctgccc ccgcactcc cggagccacc cggaatcctg    540
gccccccagc ccccgatgt gggctcctcg gaccctctga gcatggtggg accttcccag    600
ggccgaagcc ccagctacgc ttcc                                          624
```

<210> SEQ ID NO 2
<211> LENGTH: 181
<212> TYPE: PRT
<213> ORGANISM: Homo sapiens
<400> SEQUENCE: 2

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180
```

<210> SEQ ID NO 3
<211> LENGTH: 31
<212> TYPE: PRT
<213> ORGANISM: Homo sapiens
<400> SEQUENCE: 3

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
                20                  25                  30
```

<210> SEQ ID NO 4
<211> LENGTH: 39
<212> TYPE: PRT
<213> ORGANISM: Heloderma suspectum
<220> FEATURE:
<221> NAME/KEY: MOD_RES
<222> LOCATION: (39)..(39)
<223> OTHER INFORMATION: Xaa at position 39 is amidated
<220> FEATURE:
<221> NAME/KEY: MISC_FEATURE
<222> LOCATION: (39)..(39)

<223> OTHER INFORMATION: Xaa at position 39 is Ser

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Xaa
        35

<210> SEQ ID NO 5
<211> LENGTH: 230
<212> TYPE: PRT
<213> ORGANISM: Homo sapiens

<400> SEQUENCE: 5

Ala Glu Ser Lys Tyr Gly Pro Pro Cys Pro Ser Cys Pro Ala Pro Glu
1               5                   10                  15

Phe Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
        195                 200                 205

Ser Val Met His Glu Ala Leu His Asn His Tyr Thr Gln Lys Ser Leu
    210                 215                 220

Ser Leu Ser Leu Gly Lys
225                 230

<210> SEQ ID NO 6
<211> LENGTH: 15
<212> TYPE: PRT
<213> ORGANISM: Artificial Sequence
<220> FEATURE:
<223> OTHER INFORMATION: Synthetic Construct

<400> SEQUENCE: 6

Gly Gly Gly Gly Ser Gly Gly Gly Ser Gly Gly Gly Gly Ser
1               5                   10                  15

```
<210> SEQ ID NO 7
<211> LENGTH: 22
<212> TYPE: PRT
<213> ORGANISM: Artificial Sequence
<220> FEATURE:
<223> OTHER INFORMATION: Synthetic Construct

<400> SEQUENCE: 7

Gly Ser Gly Gly Gly Gly Ser Gly Gly Gly Ser Gly Gly Gly
1               5                   10                  15

Ser Gly Gly Gly Gly Ser
            20

<210> SEQ ID NO 8
<211> LENGTH: 30
<212> TYPE: PRT
<213> ORGANISM: Artificial Sequence
<220> FEATURE:
<223> OTHER INFORMATION: Synthetic Construct

<400> SEQUENCE: 8

Gly Gly Gly Gly Ser Gly Gly Gly Ser Gly Gly Gly Ser Gly
1               5                   10                  15

Gly Gly Ser Gly Gly Gly Ser Gly Gly Gly Ser
            20                  25                  30

<210> SEQ ID NO 9
<211> LENGTH: 181
<212> TYPE: PRT
<213> ORGANISM: Artificial Sequence
<220> FEATURE:
<223> OTHER INFORMATION: Synthetic Construct

<400> SEQUENCE: 9

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Cys Ala Cys Ser Phe Arg
            85                  90                  95

Glu Leu Leu Leu Glu Asp Gly Tyr Asn Val Tyr Gln Ser Glu Ala His
            100                 105                 110

Gly Leu Pro Leu His Cys Pro Gly Asn Lys Ser Pro His Arg Asp Pro
        115                 120                 125

Ala Pro Arg Gly Pro Cys Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 10
<211> LENGTH: 181
```

```
<212> TYPE: PRT
<213> ORGANISM: Artificial Sequence
<220> FEATURE:
<223> OTHER INFORMATION: Synthetic Construct

<400> SEQUENCE: 10

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Cys Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Cys Pro Gly Asn Lys Ser Pro His Arg Asp Pro
        115                 120                 125

Ala Pro Arg Gly Pro Cys Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ala Met Val Gly Pro Ser Gln Gly Arg Ser
                165                 170                 175

Pro Ser Tyr Ala Ser
            180

<210> SEQ ID NO 11
<211> LENGTH: 181
<212> TYPE: PRT
<213> ORGANISM: Artificial Sequence
<220> FEATURE:
<223> OTHER INFORMATION: Synthetic Construct

<400> SEQUENCE: 11

His Pro Ile Pro Asp Ser Ser Pro Leu Leu Gln Phe Gly Gly Gln Val
1               5                   10                  15

Arg Gln Arg Tyr Cys Tyr Thr Asp Asp Ala Gln Gln Thr Glu Ala His
            20                  25                  30

Cys Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140
```

```
Ala Leu Pro Glu Pro Pro Gly Ile Leu Ala Pro Gln Pro Pro Asp Val
145                 150                 155                 160

Gly Ser Ser Asp Pro Leu Ala Met Val Gly Pro Ser Gln Gly Arg Ser
                165                 170                 175

Pro Ser Tyr Ala Ser
            180

<210> SEQ ID NO 12
<211> LENGTH: 181
<212> TYPE: PRT
<213> ORGANISM: Artificial Sequence
<220> FEATURE:
<223> OTHER INFORMATION: Synthetic Construct

<400> SEQUENCE: 12

His Pro Ile Pro Asp Ser Ser Pro Leu Leu Gln Phe Gly Gly Gln Val
1               5                   10                  15

Arg Gln Arg Tyr Leu Tyr Thr Asp Asp Cys Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Cys Ser Pro His Arg Asp Pro
        115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Ser Asp Pro Leu Ala Met Val Gly Pro Ser Gln Gly Arg Ser
                165                 170                 175

Pro Ser Tyr Ala Ser
            180

<210> SEQ ID NO 13
<211> LENGTH: 181
<212> TYPE: PRT
<213> ORGANISM: Artificial Sequence
<220> FEATURE:
<223> OTHER INFORMATION: Synthetic Construct

<400> SEQUENCE: 13

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Gln Arg Pro Asp Gly
65                  70                  75                  80
```

-continued

```
Ala Leu Tyr Gly Ser Leu His Phe Asp Pro Glu Ala Cys Ser Phe Arg
             85                  90                  95

Glu Leu Leu Leu Glu Asp Gly Tyr Asn Val Tyr Gln Ser Glu Ala His
            100                 105                 110

Gly Leu Pro Leu His Cys Pro Gly Ala Lys Ser Pro His Arg Asp Pro
        115                 120                 125

Ala Pro Arg Gly Pro Cys Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ala Met Val Gly Pro Ser Gln Gly Arg Ser
                165                 170                 175

Pro Ser Tyr Ala Ser
            180

<210> SEQ ID NO 14
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Gly, Ala, or Val
<220> FEATURE:
<221> NAME/KEY: MISC_FEATURE
<222> LOCATION: (16)..(16)
<223> OTHER INFORMATION: Xaa at position 16 is Gly, Glu, Asp, or Lys
<220> FEATURE:
<221> NAME/KEY: MISC_FEATURE
<222> LOCATION: (27)..(27)
<223> OTHER INFORMATION: Xaa at position 27 is Val or Ile
<220> FEATURE:
<221> NAME/KEY: MISC_FEATURE
<222> LOCATION: (28)..(28)
<223> OTHER INFORMATION: Xaa at position 28 is Lys or Arg
<220> FEATURE:
<221> NAME/KEY: MISC_FEATURE
<222> LOCATION: (30)..(30)
<223> OTHER INFORMATION: Xaa at position 30 is Arg or Gly
<220> FEATURE:
<221> NAME/KEY: MOD_RES
<222> LOCATION: (30)..(30)
<223> OTHER INFORMATION: Xaa at position 30 may be amidated
<220> FEATURE:
<221> NAME/KEY: MISC_FEATURE
<222> LOCATION: (31)..(31)
<223> OTHER INFORMATION: Xaa at position 31 is Gly, Pro, or is absent
<220> FEATURE:
<221> NAME/KEY: MISC_FEATURE
<222> LOCATION: (32)..(32)
<223> OTHER INFORMATION: Xaa at position 32 is Ser or absent
<220> FEATURE:
<221> NAME/KEY: MISC_FEATURE
<222> LOCATION: (33)..(33)
<223> OTHER INFORMATION: Xaa at position 33 is Ser or absent
<220> FEATURE:
<221> NAME/KEY: MISC_FEATURE
<222> LOCATION: (34)..(34)
<223> OTHER INFORMATION: Xaa at position 34 is Gly or absent
<220> FEATURE:
<221> NAME/KEY: MISC_FEATURE
<222> LOCATION: (35)..(35)
<223> OTHER INFORMATION: Xaa at position 35 is Ala or absent
<220> FEATURE:
<221> NAME/KEY: MISC_FEATURE
<222> LOCATION: (36)..(36)
<223> OTHER INFORMATION: Xaa at position 36 is Pro or absent
<220> FEATURE:
<221> NAME/KEY: MISC_FEATURE
<222> LOCATION: (37)..(37)
<223> OTHER INFORMATION: Xaa at position 37 is Pro or absent
```

```
<220> FEATURE:
<221> NAME/KEY: MISC_FEATURE
<222> LOCATION: (38)..(38)
<223> OTHER INFORMATION: Xaa at position 38 is Pro or absent
<220> FEATURE:
<221> NAME/KEY: MISC_FEATURE
<222> LOCATION: (39)..(39)
<223> OTHER INFORMATION: Xaa at position 39 is Ser or absent

<400> SEQUENCE: 14

His Xaa Glu Gly Thr Phe Thr Ser Asp Val Ser Ser Tyr Leu Glu Xaa
1               5                   10                  15

Gln Ala Ala Lys Glu Phe Ile Ala Trp Leu Xaa Xaa Gly Xaa Xaa Xaa
            20                  25                  30

Xaa Xaa Xaa Xaa Xaa Xaa Xaa
        35

<210> SEQ ID NO 15
<211> LENGTH: 31
<212> TYPE: PRT
<213> ORGANISM: Artificial Sequence
<220> FEATURE:
<223> OTHER INFORMATION: Synthetic Construct

<400> SEQUENCE: 15

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 16
<211> LENGTH: 31
<212> TYPE: PRT
<213> ORGANISM: Artificial Sequence
<220> FEATURE:
<223> OTHER INFORMATION: Synthetic Construct

<400> SEQUENCE: 16

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 17
<211> LENGTH: 31
<212> TYPE: PRT
<213> ORGANISM: Artificial Sequence
<220> FEATURE:
<223> OTHER INFORMATION: Synthetic Construct

<400> SEQUENCE: 17

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly
            20                  25                  30

<210> SEQ ID NO 18
<211> LENGTH: 31
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (20)..(20)
<223> OTHER INFORMATION: Xaa at position 20 is Lys
<220> FEATURE:
```

```
<221> NAME/KEY: MOD_RES
<222> LOCATION: (20)..(20)
<223> OTHER INFORMATION: Xaa at position 20 is modified by (N-epsilon-
      (gamma-Glu (N-alpha--hexadecanoyl)))

<400> SEQUENCE: 18

His Ala Glu Gly Thr Phe Thr Ser Asp Val Ser Ser Tyr Leu Glu Gly
1               5                   10                  15

Gln Ala Ala Xaa Glu Phe Ile Ala Trp Leu Val Arg Gly Arg Gly
            20                  25                  30

<210> SEQ ID NO 19
<211> LENGTH: 39
<212> TYPE: PRT
<213> ORGANISM: Artificial Sequence
<220> FEATURE:
<223> OTHER INFORMATION: Synthetic Construct

<400> SEQUENCE: 19

His Val Glu Gly Thr Phe Thr Ser Asp Val Ser Ser Tyr Leu Glu Glu
1               5                   10                  15

Gln Ala Ala Lys Glu Phe Ile Ala Trp Leu Ile Lys Gly Gly Pro Ser
            20                  25                  30

Ser Gly Ala Pro Pro Pro Ser
        35

<210> SEQ ID NO 20
<211> LENGTH: 40
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is D-Ala, Gly, Val, Leu, Ile,
      Ser, or Thr
<220> FEATURE:
<221> NAME/KEY: MISC_FEATURE
<222> LOCATION: (16)..(16)
<223> OTHER INFORMATION: Xaa at position 16 is Gly, Glu, Asp, or Lys
<220> FEATURE:
<221> NAME/KEY: MISC_FEATURE
<222> LOCATION: (27)..(27)
<223> OTHER INFORMATION: Xaa at position 27 is Val or Ile
<220> FEATURE:
<221> NAME/KEY: MISC_FEATURE
<222> LOCATION: (40)..(40)
<223> OTHER INFORMATION: Xaa at position 40 is Cys
<220> FEATURE:
<221> NAME/KEY: MOD_RES
<222> LOCATION: (40)..(40)
<223> OTHER INFORMATION: Xaa at position 40 may be amidated

<400> SEQUENCE: 20

His Xaa Glu Gly Thr Phe Thr Ser Asp Val Ser Ser Tyr Leu Glu Xaa
1               5                   10                  15

Gln Ala Ala Lys Glu Phe Ile Ala Trp Leu Xaa Lys Gly Gly Pro Ser
            20                  25                  30

Ser Gly Ala Pro Pro Pro Cys Xaa
        35                  40

<210> SEQ ID NO 21
<211> LENGTH: 40
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MISC_FEATURE
<222> LOCATION: (40)..(40)
<223> OTHER INFORMATION: Xaa at position 40 is Cys
<220> FEATURE:
<221> NAME/KEY: MOD_RES
<222> LOCATION: (40)..(40)
<223> OTHER INFORMATION: Xaa at position 40 is amidated

<400> SEQUENCE: 21

His Val Glu Gly Thr Phe Thr Ser Asp Val Ser Ser Tyr Leu Glu Glu
1               5                   10                  15

Gln Ala Ala Lys Glu Phe Ile Ala Trp Leu Ile Lys Gly Gly Pro Ser
            20                  25                  30

Ser Gly Ala Pro Pro Pro Cys Xaa
        35                  40

<210> SEQ ID NO 22
<211> LENGTH: 31
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Gly or Val
<220> FEATURE:
<221> NAME/KEY: MISC_FEATURE
<222> LOCATION: (27)..(27)
<223> OTHER INFORMATION: Xaa at position 27 is Val or Lys
<220> FEATURE:
<221> NAME/KEY: MISC_FEATURE
<222> LOCATION: (28)..(28)
<223> OTHER INFORMATION: Xaa at position 28 is Lys or Asn
<220> FEATURE:
<221> NAME/KEY: MISC_FEATURE
<222> LOCATION: (31)..(31)
<223> OTHER INFORMATION: Xaa at position 31 is Gly, Pro or is absent

<400> SEQUENCE: 22

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Xaa Xaa Gly Gly Xaa
            20                  25                  30

<210> SEQ ID NO 23
<211> LENGTH: 230
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (16)..(16)
<223> OTHER INFORMATION: Xaa at position 16 is Pro or Glu
<220> FEATURE:
<221> NAME/KEY: MISC_FEATURE
<222> LOCATION: (17)..(17)
<223> OTHER INFORMATION: Xaa at position 17 is Phe, Val, or Ala
<220> FEATURE:
<221> NAME/KEY: MISC_FEATURE
<222> LOCATION: (18)..(18)
<223> OTHER INFORMATION: Xaa at position 18 is Leu, Glu, or Ala
<220> FEATURE:
<221> NAME/KEY: MISC_FEATURE
<222> LOCATION: (80)..(80)
<223> OTHER INFORMATION: Xaa at position 80 is Asn or Ala
<220> FEATURE:
<221> NAME/KEY: MISC_FEATURE
<222> LOCATION: (230)..(230)
<223> OTHER INFORMATION: Xaa at position 230 is Lys or is absent

<400> SEQUENCE: 23
```

Ala Glu Ser Lys Tyr Gly Pro Pro Cys Pro Pro Cys Pro Ala Pro Xaa
1               5                   10                  15

Xaa Xaa Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
50                  55                  60

Val Glu Val His Asn Ala Lys Thr Lys Pro Arg Glu Glu Gln Phe Xaa
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
                100                 105                 110

Ser Ser Ile Glu Lys Thr Ile Ser Lys Ala Lys Gly Gln Pro Arg Glu
                115                 120                 125

Pro Gln Val Tyr Thr Leu Pro Pro Ser Gln Glu Glu Met Thr Lys Asn
130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
                180                 185                 190

Leu Thr Val Asp Lys Ser Arg Trp Gln Glu Gly Asn Val Phe Ser Cys
                195                 200                 205

Ser Val Met His Glu Ala Leu His Asn His Tyr Thr Gln Lys Ser Leu
        210                 215                 220

Ser Leu Ser Leu Gly Xaa
225                 230

<210> SEQ ID NO 24
<211> LENGTH: 276
<212> TYPE: PRT
<213> ORGANISM: Artificial Sequence
<220> FEATURE:
<223> OTHER INFORMATION: Synthetic Construct

<400> SEQUENCE: 24

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Ser Ala Glu
        35                  40                  45                  Glu

Ser Lys Tyr Gly Pro Pro Cys Pro Pro Cys Pro Ala Pro Glu Phe Leu
        50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
                100                 105                 110

Val His Asn Ala Lys Thr Lys Pro Arg Glu Glu Gln Phe Asn Ser Thr
                115                 120                 125

```
Tyr Arg Val Val Ser Val Leu Thr Val Leu His Gln Asp Trp Leu Asn
        130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Lys
        275

<210> SEQ ID NO 25
<211> LENGTH: 276
<212> TYPE: PRT
<213> ORGANISM: Artificial Sequence
<220> FEATURE:
<223> OTHER INFORMATION: Synthetic Construct

<400> SEQUENCE: 25

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Gly Ser Ala Glu
        35                  40                  45

Ser Lys Tyr Gly Pro Pro Cys Pro Pro Cys Pro Ala Pro Glu Ala Ala
50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
```

```
                210                 215                 220
Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
                260                 265                 270

Ser Leu Gly Lys
        275

<210> SEQ ID NO 26
<211> LENGTH: 276
<212> TYPE: PRT
<213> ORGANISM: Artificial Sequence
<220> FEATURE:
<223> OTHER INFORMATION: Synthetic Construct

<400> SEQUENCE: 26

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ser Gly Gly Gly Ser Gly Gly Gly Ser Ala Glu
            35                  40                  45

Ser Lys Tyr Gly Pro Pro Cys Pro Pro Cys Pro Ala Pro Glu Phe Leu
50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
                100                 105                 110

Val His Asn Ala Lys Thr Lys Pro Arg Glu Glu Gln Phe Ala Ser Thr
            115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
                260                 265                 270

Ser Leu Gly Lys
        275

<210> SEQ ID NO 27
```

```
<211> LENGTH: 276
<212> TYPE: PRT
<213> ORGANISM: Artificial Sequence
<220> FEATURE:
<223> OTHER INFORMATION: Synthetic Construct

<400> SEQUENCE: 27

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Ser Ala Glu
        35                  40                  45

Ser Lys Tyr Gly Pro Pro Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Ala Ser Thr
        115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Lys
    275

<210> SEQ ID NO 28
<211> LENGTH: 275
<212> TYPE: PRT
<213> ORGANISM: Artificial Sequence
<220> FEATURE:
<223> OTHER INFORMATION: Synthetic Construct

<400> SEQUENCE: 28

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Ser Ala Glu
        35                  40                  45
```

```
Ser Lys Tyr Gly Pro Pro Cys Pro Cys Pro Ala Pro Glu Phe Leu
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly
        275

<210> SEQ ID NO 29
<211> LENGTH: 275
<212> TYPE: PRT
<213> ORGANISM: Artificial Sequence
<220> FEATURE:
<223> OTHER INFORMATION: Synthetic Construct

<400> SEQUENCE: 29

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Ser Ala Glu
        35                  40                  45

Ser Lys Tyr Gly Pro Pro Cys Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125
```

```
Tyr Arg Val Val Ser Val Leu Thr Val Leu His Gln Asp Trp Leu Asn
        130                 135                 140
Gly Lys Glu Tyr Lys Cys Lys Val Ser Asn Lys Gly Leu Pro Ser Ser
145                 150                 155                 160
Ile Glu Lys Thr Ile Ser Lys Ala Lys Gly Gln Pro Arg Glu Pro Gln
                165                 170                 175
Val Tyr Thr Leu Pro Pro Ser Gln Glu Glu Met Thr Lys Asn Gln Val
            180                 185                 190
Ser Leu Thr Cys Leu Val Lys Gly Phe Tyr Pro Ser Asp Ile Ala Val
        195                 200                 205
Glu Trp Glu Ser Asn Gly Gln Pro Glu Asn Asn Tyr Lys Thr Thr Pro
    210                 215                 220
Pro Val Leu Asp Ser Asp Gly Ser Phe Phe Leu Tyr Ser Arg Leu Thr
225                 230                 235                 240
Val Asp Lys Ser Arg Trp Gln Glu Gly Asn Val Phe Ser Cys Ser Val
                245                 250                 255
Met His Glu Ala Leu His Asn His Tyr Thr Gln Lys Ser Leu Ser Leu
            260                 265                 270
Ser Leu Gly
        275

<210> SEQ ID NO 30
<211> LENGTH: 275
<212> TYPE: PRT
<213> ORGANISM: Artificial Sequence
<220> FEATURE:
<223> OTHER INFORMATION: Synthetic Construct

<400> SEQUENCE: 30

His Gly Glu Gly Thr Phe Thr Ser Asp Val Ser Ser Tyr Leu Glu Glu
1               5                   10                  15
Gln Ala Ala Lys Glu Phe Ile Ala Trp Leu Val Lys Gly Gly Gly Gly
            20                  25                  30
Gly Gly Gly Ser Gly Gly Gly Ser Gly Gly Gly Ser Ala Glu
        35                  40                  45
Ser Lys Tyr Gly Pro Pro Cys Pro Pro Cys Pro Ala Pro Glu Phe Leu
    50                  55                  60
Gly Gly Pro Ser Val Phe Leu Phe Pro Pro Lys Pro Lys Asp Thr Leu
65                  70                  75                  80
Met Ile Ser Arg Thr Pro Glu Val Thr Cys Val Val Val Asp Val Ser
                85                  90                  95
Gln Glu Asp Pro Glu Val Gln Phe Asn Trp Tyr Val Asp Gly Val Glu
            100                 105                 110
Val His Asn Ala Lys Thr Lys Pro Arg Glu Glu Gln Phe Ala Ser Thr
        115                 120                 125
Tyr Arg Val Val Ser Val Leu Thr Val Leu His Gln Asp Trp Leu Asn
    130                 135                 140
Gly Lys Glu Tyr Lys Cys Lys Val Ser Asn Lys Gly Leu Pro Ser Ser
145                 150                 155                 160
Ile Glu Lys Thr Ile Ser Lys Ala Lys Gly Gln Pro Arg Glu Pro Gln
                165                 170                 175
Val Tyr Thr Leu Pro Pro Ser Gln Glu Glu Met Thr Lys Asn Gln Val
            180                 185                 190
Ser Leu Thr Cys Leu Val Lys Gly Phe Tyr Pro Ser Asp Ile Ala Val
        195                 200                 205
Glu Trp Glu Ser Asn Gly Gln Pro Glu Asn Asn Tyr Lys Thr Thr Pro
```

```
                       210                 215                 220
Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
                260                 265                 270

Ser Leu Gly
        275

<210> SEQ ID NO 31
<211> LENGTH: 275
<212> TYPE: PRT
<213> ORGANISM: Artificial Sequence
<220> FEATURE:
<223> OTHER INFORMATION: Synthetic Construct

<400> SEQUENCE: 31

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ser Gly Gly Gly Ser Gly Gly Gly Ser Ala Glu
            35                  40                  45

Ser Lys Tyr Gly Pro Pro Cys Pro Pro Cys Pro Ala Pro Glu Ala Ala
50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
                100                 105                 110

Val His Asn Ala Lys Thr Lys Pro Arg Glu Glu Gln Phe Ala Ser Thr
            115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
                180                 185                 190

Ser Leu Thr Cys Leu Val Lys Gly Phe Tyr Pro Ser Asp Ile Ala Val
            195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
                260                 265                 270

Ser Leu Gly
        275

<210> SEQ ID NO 32
```

```
<211> LENGTH: 283
<212> TYPE: PRT
<213> ORGANISM: Artificial Sequence
<220> FEATURE:
<223> OTHER INFORMATION: Synthetic Construct

<400> SEQUENCE: 32

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Ser Gly Gly Gly Gly Ser Gly Gly Gly Ser Gly Gly Gly Gly Ser
        35                  40                  45

Gly Gly Gly Ser Ala Glu Ser Lys Tyr Gly Pro Pro Cys Pro Pro
50                  55                  60

Cys Pro Ala Pro Glu Phe Leu Gly Gly Pro Ser Val Phe Leu Phe Pro
65                  70                  75                  80

Pro Lys Pro Lys Asp Thr Leu Met Ile Ser Arg Thr Pro Glu Val Thr
                85                  90                  95

Cys Val Val Val Asp Val Ser Gln Glu Asp Pro Glu Val Gln Phe Asn
            100                 105                 110

Trp Tyr Val Asp Gly Val Glu Val His Asn Ala Lys Thr Lys Pro Arg
        115                 120                 125

Glu Glu Gln Phe Asn Ser Thr Tyr Arg Val Val Ser Val Leu Thr Val
130                 135                 140

Leu His Gln Asp Trp Leu Asn Gly Lys Glu Tyr Lys Cys Lys Val Ser
145                 150                 155                 160

Asn Lys Gly Leu Pro Ser Ser Ile Glu Lys Thr Ile Ser Lys Ala Lys
                165                 170                 175

Gly Gln Pro Arg Glu Pro Gln Val Tyr Thr Leu Pro Pro Ser Gln Glu
            180                 185                 190

Glu Met Thr Lys Asn Gln Val Ser Leu Thr Cys Leu Val Lys Gly Phe
        195                 200                 205

Tyr Pro Ser Asp Ile Ala Val Glu Trp Glu Ser Asn Gly Gln Pro Glu
210                 215                 220

Asn Asn Tyr Lys Thr Thr Pro Pro Val Leu Asp Ser Asp Gly Ser Phe
225                 230                 235                 240

Phe Leu Tyr Ser Arg Leu Thr Val Asp Lys Ser Arg Trp Gln Glu Gly
                245                 250                 255

Asn Val Phe Ser Cys Ser Val Met His Glu Ala Leu His Asn His Tyr
            260                 265                 270

Thr Gln Lys Ser Leu Ser Leu Ser Leu Gly Lys
        275                 280

<210> SEQ ID NO 33
<211> LENGTH: 283
<212> TYPE: PRT
<213> ORGANISM: Artificial Sequence
<220> FEATURE:
<223> OTHER INFORMATION: Synthetic Construct

<400> SEQUENCE: 33

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Ser Gly Gly Gly Gly Ser Gly Gly Gly Gly Ser Gly Gly Gly Gly Ser
        35                  40                  45
```

```
Gly Gly Gly Gly Ser Ala Glu Ser Lys Tyr Gly Pro Pro Cys Pro Pro
        50                  55                  60

Cys Pro Ala Pro Glu Ala Ala Gly Gly Pro Ser Val Phe Leu Phe Pro
 65              70                  75                  80

Pro Lys Pro Lys Asp Thr Leu Met Ile Ser Arg Thr Pro Glu Val Thr
                    85                  90                  95

Cys Val Val Val Asp Val Ser Gln Glu Asp Pro Glu Val Gln Phe Asn
                100                 105                 110

Trp Tyr Val Asp Gly Val Glu Val His Asn Ala Lys Thr Lys Pro Arg
            115                 120                 125

Glu Glu Gln Phe Asn Ser Thr Tyr Arg Val Val Ser Val Leu Thr Val
130                 135                 140

Leu His Gln Asp Trp Leu Asn Gly Lys Glu Tyr Lys Cys Lys Val Ser
145                 150                 155                 160

Asn Lys Gly Leu Pro Ser Ser Ile Glu Lys Thr Ile Ser Lys Ala Lys
                165                 170                 175

Gly Gln Pro Arg Glu Pro Gln Val Tyr Thr Leu Pro Pro Ser Gln Glu
            180                 185                 190

Glu Met Thr Lys Asn Gln Val Ser Leu Thr Cys Leu Val Lys Gly Phe
        195                 200                 205

Tyr Pro Ser Asp Ile Ala Val Glu Trp Glu Ser Asn Gly Gln Pro Glu
210                 215                 220

Asn Asn Tyr Lys Thr Thr Pro Pro Val Leu Asp Ser Asp Gly Ser Phe
225                 230                 235                 240

Phe Leu Tyr Ser Arg Leu Thr Val Asp Lys Ser Arg Trp Gln Glu Gly
                245                 250                 255

Asn Val Phe Ser Cys Ser Val Met His Glu Ala Leu His Asn His Tyr
            260                 265                 270

Thr Gln Lys Ser Leu Ser Leu Ser Leu Gly Lys
        275                 280

<210> SEQ ID NO 34
<211> LENGTH: 283
<212> TYPE: PRT
<213> ORGANISM: Artificial Sequence
<220> FEATURE:
<223> OTHER INFORMATION: Synthetic Construct

<400> SEQUENCE: 34

His Gly Glu Gly Thr Phe Thr Ser Asp Val Ser Ser Tyr Leu Glu Glu
 1               5                  10                  15

Gln Ala Ala Lys Glu Phe Ile Ala Trp Leu Val Lys Gly Gly Gly Gly
                20                  25                  30

Ser Gly Gly Gly Gly Ser Gly Gly Gly Ser Gly Gly Gly Gly Ser
            35                  40                  45

Gly Gly Gly Gly Ser Ala Glu Ser Lys Tyr Gly Pro Pro Cys Pro Pro
        50                  55                  60

Cys Pro Ala Pro Glu Phe Leu Gly Gly Pro Ser Val Phe Leu Phe Pro
 65              70                  75                  80

Pro Lys Pro Lys Asp Thr Leu Met Ile Ser Arg Thr Pro Glu Val Thr
                    85                  90                  95

Cys Val Val Val Asp Val Ser Gln Glu Asp Pro Glu Val Gln Phe Asn
                100                 105                 110

Trp Tyr Val Asp Gly Val Glu Val His Asn Ala Lys Thr Lys Pro Arg
            115                 120                 125
```

```
Glu Glu Gln Phe Ala Ser Thr Tyr Arg Val Val Ser Val Leu Thr Val
        130                 135                 140

Leu His Gln Asp Trp Leu Asn Gly Lys Glu Tyr Lys Cys Lys Val Ser
145                 150                 155                 160

Asn Lys Gly Leu Pro Ser Ser Ile Glu Lys Thr Ile Ser Lys Ala Lys
                165                 170                 175

Gly Gln Pro Arg Glu Pro Gln Val Tyr Thr Leu Pro Pro Ser Gln Glu
                180                 185                 190

Glu Met Thr Lys Asn Gln Val Ser Leu Thr Cys Leu Val Lys Gly Phe
                195                 200                 205

Tyr Pro Ser Asp Ile Ala Val Glu Trp Glu Ser Asn Gly Gln Pro Glu
                210                 215                 220

Asn Asn Tyr Lys Thr Thr Pro Pro Val Leu Asp Ser Asp Gly Ser Phe
225                 230                 235                 240

Phe Leu Tyr Ser Arg Leu Thr Val Asp Lys Ser Arg Trp Gln Glu Gly
                245                 250                 255

Asn Val Phe Ser Cys Ser Val Met His Glu Ala Leu His Asn His Tyr
                260                 265                 270

Thr Gln Lys Ser Leu Ser Leu Ser Leu Gly Lys
                275                 280

<210> SEQ ID NO 35
<211> LENGTH: 283
<212> TYPE: PRT
<213> ORGANISM: Artificial Sequence
<220> FEATURE:
<223> OTHER INFORMATION: Synthetic Construct

<400> SEQUENCE: 35

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Ser Gly Gly Gly Gly Ser Gly Gly Gly Gly Ser Gly Gly Gly Gly Ser
                35                  40                  45

Gly Gly Gly Gly Ser Ala Glu Ser Lys Tyr Gly Pro Pro Cys Pro Pro
50                  55                  60

Cys Pro Ala Pro Glu Ala Ala Gly Gly Pro Ser Val Phe Leu Phe Pro
65                  70                  75                  80

Pro Lys Pro Lys Asp Thr Leu Met Ile Ser Arg Thr Pro Glu Val Thr
                85                  90                  95

Cys Val Val Val Asp Val Ser Gln Glu Asp Pro Glu Val Gln Phe Asn
                100                 105                 110

Trp Tyr Val Asp Gly Val Glu Val His Asn Ala Lys Thr Lys Pro Arg
                115                 120                 125

Glu Glu Gln Phe Ala Ser Thr Tyr Arg Val Val Ser Val Leu Thr Val
        130                 135                 140

Leu His Gln Asp Trp Leu Asn Gly Lys Glu Tyr Lys Cys Lys Val Ser
145                 150                 155                 160

Asn Lys Gly Leu Pro Ser Ser Ile Glu Lys Thr Ile Ser Lys Ala Lys
                165                 170                 175

Gly Gln Pro Arg Glu Pro Gln Val Tyr Thr Leu Pro Pro Ser Gln Glu
                180                 185                 190

Glu Met Thr Lys Asn Gln Val Ser Leu Thr Cys Leu Val Lys Gly Phe
                195                 200                 205

Tyr Pro Ser Asp Ile Ala Val Glu Trp Glu Ser Asn Gly Gln Pro Glu
```

Asn Asn Tyr Lys Thr Thr Pro Pro Val Leu Asp Ser Asp Gly Ser Phe
225                 230                 235                 240

Phe Leu Tyr Ser Arg Leu Thr Val Asp Lys Ser Arg Trp Gln Glu Gly
            245                 250                 255

Asn Val Phe Ser Cys Ser Val Met His Glu Ala Leu His Asn His Tyr
            260                 265                 270

Thr Gln Lys Ser Leu Ser Leu Ser Leu Gly Lys
        275                 280

<210> SEQ ID NO 36
<211> LENGTH: 282
<212> TYPE: PRT
<213> ORGANISM: Artificial Sequence
<220> FEATURE:
<223> OTHER INFORMATION: Synthetic Construct

<400> SEQUENCE: 36

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Ser Gly Gly Gly Gly Ser Gly Gly Gly Gly Ser Gly Gly Gly Gly Ser
        35                  40                  45

Gly Gly Gly Gly Ser Ala Glu Ser Lys Tyr Gly Pro Pro Cys Pro Pro
    50                  55                  60

Cys Pro Ala Pro Glu Phe Leu Gly Gly Pro Ser Val Phe Leu Phe Pro
65                  70                  75                  80

Pro Lys Pro Lys Asp Thr Leu Met Ile Ser Arg Thr Pro Glu Val Thr
                85                  90                  95

Cys Val Val Val Asp Val Ser Gln Glu Asp Pro Glu Val Gln Phe Asn
            100                 105                 110

Trp Tyr Val Asp Gly Val Glu Val His Asn Ala Lys Thr Lys Pro Arg
        115                 120                 125

Glu Glu Gln Phe Asn Ser Thr Tyr Arg Val Val Ser Val Leu Thr Val
    130                 135                 140

Leu His Gln Asp Trp Leu Asn Gly Lys Glu Tyr Lys Cys Lys Val Ser
145                 150                 155                 160

Asn Lys Gly Leu Pro Ser Ser Ile Glu Lys Thr Ile Ser Lys Ala Lys
                165                 170                 175

Gly Gln Pro Arg Glu Pro Gln Val Tyr Thr Leu Pro Pro Ser Gln Glu
            180                 185                 190

Glu Met Thr Lys Asn Gln Val Ser Leu Thr Cys Leu Val Lys Gly Phe
        195                 200                 205

Tyr Pro Ser Asp Ile Ala Val Glu Trp Glu Ser Asn Gly Gln Pro Glu
    210                 215                 220

Asn Asn Tyr Lys Thr Thr Pro Pro Val Leu Asp Ser Asp Gly Ser Phe
225                 230                 235                 240

Phe Leu Tyr Ser Arg Leu Thr Val Asp Lys Ser Arg Trp Gln Glu Gly
                245                 250                 255

Asn Val Phe Ser Cys Ser Val Met His Glu Ala Leu His Asn His Tyr
            260                 265                 270

Thr Gln Lys Ser Leu Ser Leu Ser Leu Gly
        275                 280

<210> SEQ ID NO 37

```
<211> LENGTH: 282
<212> TYPE: PRT
<213> ORGANISM: Artificial Sequence
<220> FEATURE:
<223> OTHER INFORMATION: Synthetic Construct

<400> SEQUENCE: 37

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Ser Gly Gly Gly Gly Ser Gly Gly Gly Ser Gly Gly Gly Gly Ser
        35                  40                  45

Gly Gly Gly Gly Ser Ala Glu Ser Lys Tyr Gly Pro Pro Cys Pro Pro
    50                  55                  60

Cys Pro Ala Pro Glu Ala Ala Gly Gly Pro Ser Val Phe Leu Phe Pro
65                  70                  75                  80

Pro Lys Pro Lys Asp Thr Leu Met Ile Ser Arg Thr Pro Glu Val Thr
                85                  90                  95

Cys Val Val Val Asp Val Ser Gln Glu Asp Pro Glu Val Gln Phe Asn
            100                 105                 110

Trp Tyr Val Asp Gly Val Glu Val His Asn Ala Lys Thr Lys Pro Arg
        115                 120                 125

Glu Glu Gln Phe Asn Ser Thr Tyr Arg Val Val Ser Val Leu Thr Val
    130                 135                 140

Leu His Gln Asp Trp Leu Asn Gly Lys Glu Tyr Lys Cys Lys Val Ser
145                 150                 155                 160

Asn Lys Gly Leu Pro Ser Ser Ile Glu Lys Thr Ile Ser Lys Ala Lys
                165                 170                 175

Gly Gln Pro Arg Glu Pro Gln Val Tyr Thr Leu Pro Pro Ser Gln Glu
            180                 185                 190

Glu Met Thr Lys Asn Gln Val Ser Leu Thr Cys Leu Val Lys Gly Phe
        195                 200                 205

Tyr Pro Ser Asp Ile Ala Val Glu Trp Glu Ser Asn Gly Gln Pro Glu
    210                 215                 220

Asn Asn Tyr Lys Thr Thr Pro Pro Val Leu Asp Ser Asp Gly Ser Phe
225                 230                 235                 240

Phe Leu Tyr Ser Arg Leu Thr Val Asp Lys Ser Arg Trp Gln Glu Gly
                245                 250                 255

Asn Val Phe Ser Cys Ser Val Met His Glu Ala Leu His Asn His Tyr
            260                 265                 270

Thr Gln Lys Ser Leu Ser Leu Ser Leu Gly
        275                 280

<210> SEQ ID NO 38
<211> LENGTH: 282
<212> TYPE: PRT
<213> ORGANISM: Artificial Sequence
<220> FEATURE:
<223> OTHER INFORMATION: Synthetic Construct

<400> SEQUENCE: 38

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Ser Gly Gly Gly Gly Ser Gly Gly Gly Gly Ser Gly Gly Gly Gly Ser
        35                  40                  45
```

```
Gly Gly Gly Gly Ser Ala Glu Ser Lys Tyr Gly Pro Pro Cys Pro Pro
            50                  55                  60

Cys Pro Ala Pro Glu Phe Leu Gly Gly Pro Ser Val Phe Leu Phe Pro
 65                  70                  75                  80

Pro Lys Pro Lys Asp Thr Leu Met Ile Ser Arg Thr Pro Glu Val Thr
                 85                  90                  95

Cys Val Val Val Asp Val Ser Gln Glu Asp Pro Glu Val Gln Phe Asn
            100                 105                 110

Trp Tyr Val Asp Gly Val Glu Val His Asn Ala Lys Thr Lys Pro Arg
            115                 120                 125

Glu Glu Gln Phe Ala Ser Thr Tyr Arg Val Val Ser Val Leu Thr Val
130                 135                 140

Leu His Gln Asp Trp Leu Asn Gly Lys Glu Tyr Lys Cys Lys Val Ser
145                 150                 155                 160

Asn Lys Gly Leu Pro Ser Ser Ile Glu Lys Thr Ile Ser Lys Ala Lys
                165                 170                 175

Gly Gln Pro Arg Glu Pro Gln Val Tyr Thr Leu Pro Pro Ser Gln Glu
            180                 185                 190

Glu Met Thr Lys Asn Gln Val Ser Leu Thr Cys Leu Val Lys Gly Phe
            195                 200                 205

Tyr Pro Ser Asp Ile Ala Val Glu Trp Glu Ser Asn Gly Gln Pro Glu
210                 215                 220

Asn Asn Tyr Lys Thr Thr Pro Pro Val Leu Asp Ser Asp Gly Ser Phe
225                 230                 235                 240

Phe Leu Tyr Ser Arg Leu Thr Val Asp Lys Ser Arg Trp Gln Glu Gly
                245                 250                 255

Asn Val Phe Ser Cys Ser Val Met His Glu Ala Leu His Asn His Tyr
            260                 265                 270

Thr Gln Lys Ser Leu Ser Leu Ser Leu Gly
            275                 280

<210> SEQ ID NO 39
<211> LENGTH: 282
<212> TYPE: PRT
<213> ORGANISM: Artificial Sequence
<220> FEATURE:
<223> OTHER INFORMATION: Synthetic Construct

<400> SEQUENCE: 39

His Gly Glu Gly Thr Phe Thr Ser Asp Val Ser Ser Tyr Leu Glu Glu
  1               5                  10                  15

Gln Ala Ala Lys Glu Phe Ile Ala Trp Leu Val Lys Gly Gly Gly Gly
                 20                  25                  30

Ser Gly Gly Gly Gly Ser Gly Gly Gly Gly Ser Gly Gly Gly Gly Ser
             35                  40                  45

Gly Gly Gly Gly Ser Ala Glu Ser Lys Tyr Gly Pro Pro Cys Pro Pro
            50                  55                  60

Cys Pro Ala Pro Glu Ala Ala Gly Gly Pro Ser Val Phe Leu Phe Pro
 65                  70                  75                  80

Pro Lys Pro Lys Asp Thr Leu Met Ile Ser Arg Thr Pro Glu Val Thr
                 85                  90                  95

Cys Val Val Val Asp Val Ser Gln Glu Asp Pro Glu Val Gln Phe Asn
            100                 105                 110

Trp Tyr Val Asp Gly Val Glu Val His Asn Ala Lys Thr Lys Pro Arg
            115                 120                 125
```

Glu Glu Gln Phe Ala Ser Thr Tyr Arg Val Val Ser Val Leu Thr Val
130                 135                 140

Leu His Gln Asp Trp Leu Asn Gly Lys Glu Tyr Lys Cys Lys Val Ser
145                 150                 155                 160

Asn Lys Gly Leu Pro Ser Ser Ile Glu Lys Thr Ile Ser Lys Ala Lys
                165                 170                 175

Gly Gln Pro Arg Glu Pro Gln Val Tyr Thr Leu Pro Pro Ser Gln Glu
            180                 185                 190

Glu Met Thr Lys Asn Gln Val Ser Leu Thr Cys Leu Val Lys Gly Phe
        195                 200                 205

Tyr Pro Ser Asp Ile Ala Val Glu Trp Glu Ser Asn Gly Gln Pro Glu
    210                 215                 220

Asn Asn Tyr Lys Thr Thr Pro Pro Val Leu Asp Ser Asp Gly Ser Phe
225                 230                 235                 240

Phe Leu Tyr Ser Arg Leu Thr Val Asp Lys Ser Arg Trp Gln Glu Gly
                245                 250                 255

Asn Val Phe Ser Cys Ser Val Met His Glu Ala Leu His Asn His Tyr
                260                 265                 270

Thr Gln Lys Ser Leu Ser Leu Ser Leu Gly
            275                 280

<210> SEQ ID NO 40
<211> LENGTH: 291
<212> TYPE: PRT
<213> ORGANISM: Artificial Sequence
<220> FEATURE:
<223> OTHER INFORMATION: Synthetic Construct

<400> SEQUENCE: 40

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Ser Gly Gly
        35                  40                  45

Gly Gly Ser Gly Gly Gly Ser Gly Gly Gly Ser Ala Glu Ser
50                  55                  60

Lys Tyr Gly Pro Pro Cys Pro Pro Cys Pro Ala Pro Glu Phe Leu Gly
65                  70                  75                  80

Gly Pro Ser Val Phe Leu Phe Pro Pro Lys Pro Lys Asp Thr Leu Met
                85                  90                  95

Ile Ser Arg Thr Pro Glu Val Thr Cys Val Val Val Asp Val Ser Gln
            100                 105                 110

Glu Asp Pro Glu Val Gln Phe Asn Trp Tyr Val Asp Gly Val Glu Val
        115                 120                 125

His Asn Ala Lys Thr Lys Pro Arg Glu Glu Gln Phe Asn Ser Thr Tyr
130                 135                 140

Arg Val Val Ser Val Leu Thr Val Leu His Gln Asp Trp Leu Asn Gly
145                 150                 155                 160

Lys Glu Tyr Lys Cys Lys Val Ser Asn Lys Gly Leu Pro Ser Ser Ile
                165                 170                 175

Glu Lys Thr Ile Ser Lys Ala Lys Gly Gln Pro Arg Glu Pro Gln Val
            180                 185                 190

Tyr Thr Leu Pro Pro Ser Gln Glu Glu Met Thr Lys Asn Gln Val Ser
        195                 200                 205

Leu Thr Cys Leu Val Lys Gly Phe Tyr Pro Ser Asp Ile Ala Val Glu

```
            210                 215                 220
Trp Glu Ser Asn Gly Gln Pro Glu Asn Asn Tyr Lys Thr Thr Pro Pro
225                 230                 235                 240

Val Leu Asp Ser Asp Gly Ser Phe Phe Leu Tyr Ser Arg Leu Thr Val
                245                 250                 255

Asp Lys Ser Arg Trp Gln Glu Gly Asn Val Phe Ser Cys Ser Val Met
            260                 265                 270

His Glu Ala Leu His Asn His Tyr Thr Gln Lys Ser Leu Ser Leu Ser
        275                 280                 285

Leu Gly Lys
    290

<210> SEQ ID NO 41
<211> LENGTH: 291
<212> TYPE: PRT
<213> ORGANISM: Artificial Sequence
<220> FEATURE:
<223> OTHER INFORMATION: Synthetic Construct

<400> SEQUENCE: 41

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Ser Gly Gly Gly Gly
        35                  40                  45

Gly Gly Ser Gly Gly Gly Ser Gly Gly Gly Ser Ala Glu Ser
    50                  55                  60

Lys Tyr Gly Pro Pro Cys Pro Pro Cys Pro Ala Pro Glu Ala Ala Gly
65                  70                  75                  80

Gly Pro Ser Val Phe Leu Phe Pro Pro Lys Pro Lys Asp Thr Leu Met
                85                  90                  95

Ile Ser Arg Thr Pro Glu Val Thr Cys Val Val Val Asp Val Ser Gln
            100                 105                 110

Glu Asp Pro Glu Val Gln Phe Asn Trp Tyr Val Asp Gly Val Glu Val
        115                 120                 125

His Asn Ala Lys Thr Lys Pro Arg Glu Glu Gln Phe Asn Ser Thr Tyr
    130                 135                 140

Arg Val Val Ser Val Leu Thr Val Leu His Gln Asp Trp Leu Asn Gly
145                 150                 155                 160

Lys Glu Tyr Lys Cys Lys Val Ser Asn Lys Gly Leu Pro Ser Ser Ile
                165                 170                 175

Glu Lys Thr Ile Ser Lys Ala Lys Gly Gln Pro Arg Glu Pro Gln Val
            180                 185                 190

Tyr Thr Leu Pro Pro Ser Gln Glu Glu Met Thr Lys Asn Gln Val Ser
        195                 200                 205

Leu Thr Cys Leu Val Lys Gly Phe Tyr Pro Ser Asp Ile Ala Val Glu
    210                 215                 220

Trp Glu Ser Asn Gly Gln Pro Glu Asn Asn Tyr Lys Thr Thr Pro Pro
225                 230                 235                 240

Val Leu Asp Ser Asp Gly Ser Phe Phe Leu Tyr Ser Arg Leu Thr Val
                245                 250                 255

Asp Lys Ser Arg Trp Gln Glu Gly Asn Val Phe Ser Cys Ser Val Met
            260                 265                 270

His Glu Ala Leu His Asn His Tyr Thr Gln Lys Ser Leu Ser Leu Ser
        275                 280                 285
```

```
Leu Gly Lys
    290

<210> SEQ ID NO 42
<211> LENGTH: 291
<212> TYPE: PRT
<213> ORGANISM: Artificial Sequence
<220> FEATURE:
<223> OTHER INFORMATION: Synthetic Construct

<400> SEQUENCE: 42

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Ser Gly Gly Gly Ser Gly Gly Gly Ser Gly Gly
        35                  40                  45

Gly Gly Ser Gly Gly Gly Ser Gly Gly Gly Ser Ala Glu Ser
        50                  55                  60

Lys Tyr Gly Pro Pro Cys Pro Pro Cys Pro Ala Pro Glu Phe Leu Gly
65              70                  75                  80

Gly Pro Ser Val Phe Leu Phe Pro Pro Lys Pro Lys Asp Thr Leu Met
                85                  90                  95

Ile Ser Arg Thr Pro Glu Val Thr Cys Val Val Val Asp Val Ser Gln
            100                 105                 110

Glu Asp Pro Glu Val Gln Phe Asn Trp Tyr Val Asp Gly Val Glu Val
        115                 120                 125

His Asn Ala Lys Thr Lys Pro Arg Glu Glu Gln Phe Ala Ser Thr Tyr
130                 135                 140

Arg Val Val Ser Val Leu Thr Val Leu His Gln Asp Trp Leu Asn Gly
145                 150                 155                 160

Lys Glu Tyr Lys Cys Lys Val Ser Asn Lys Gly Leu Pro Ser Ser Ile
                165                 170                 175

Glu Lys Thr Ile Ser Lys Ala Lys Gly Gln Pro Arg Glu Pro Gln Val
            180                 185                 190

Tyr Thr Leu Pro Pro Ser Gln Glu Glu Met Thr Lys Asn Gln Val Ser
        195                 200                 205

Leu Thr Cys Leu Val Lys Gly Phe Tyr Pro Ser Asp Ile Ala Val Glu
    210                 215                 220

Trp Glu Ser Asn Gly Gln Pro Glu Asn Asn Tyr Lys Thr Thr Pro Pro
225                 230                 235                 240

Val Leu Asp Ser Asp Gly Ser Phe Phe Leu Tyr Ser Arg Leu Thr Val
                245                 250                 255

Asp Lys Ser Arg Trp Gln Glu Gly Asn Val Phe Ser Cys Ser Val Met
            260                 265                 270

His Glu Ala Leu His Asn His Tyr Thr Gln Lys Ser Leu Ser Leu Ser
        275                 280                 285

Leu Gly Lys
    290

<210> SEQ ID NO 43
<211> LENGTH: 291
<212> TYPE: PRT
<213> ORGANISM: Artificial Sequence
<220> FEATURE:
<223> OTHER INFORMATION: Synthetic Construct

<400> SEQUENCE: 43
```

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Ser Gly Gly
            35                  40                  45

Gly Gly Ser Gly Gly Gly Ser Gly Gly Gly Ser Ala Glu Ser
50                  55                  60

Lys Tyr Gly Pro Pro Cys Pro Pro Cys Pro Ala Pro Glu Ala Ala Gly
65                  70                  75                  80

Gly Pro Ser Val Phe Leu Phe Pro Pro Lys Pro Lys Asp Thr Leu Met
                85                  90                  95

Ile Ser Arg Thr Pro Glu Val Thr Cys Val Val Val Asp Val Ser Gln
                100                 105                 110

Glu Asp Pro Glu Val Gln Phe Asn Trp Tyr Val Asp Gly Val Glu Val
            115                 120                 125

His Asn Ala Lys Thr Lys Pro Arg Glu Glu Gln Phe Ala Ser Thr Tyr
    130                 135                 140

Arg Val Val Ser Val Leu Thr Val Leu His Gln Asp Trp Leu Asn Gly
145                 150                 155                 160

Lys Glu Tyr Lys Cys Lys Val Ser Asn Lys Gly Leu Pro Ser Ser Ile
                165                 170                 175

Glu Lys Thr Ile Ser Lys Ala Lys Gly Gln Pro Arg Glu Pro Gln Val
            180                 185                 190

Tyr Thr Leu Pro Pro Ser Gln Glu Glu Met Thr Lys Asn Gln Val Ser
        195                 200                 205

Leu Thr Cys Leu Val Lys Gly Phe Tyr Pro Ser Asp Ile Ala Val Glu
    210                 215                 220

Trp Glu Ser Asn Gly Gln Pro Glu Asn Asn Tyr Lys Thr Thr Pro Pro
225                 230                 235                 240

Val Leu Asp Ser Asp Gly Ser Phe Phe Leu Tyr Ser Arg Leu Thr Val
                245                 250                 255

Asp Lys Ser Arg Trp Gln Glu Gly Asn Val Phe Ser Cys Ser Val Met
                260                 265                 270

His Glu Ala Leu His Asn His Tyr Thr Gln Lys Ser Leu Ser Leu Ser
            275                 280                 285

Leu Gly Lys
    290

<210> SEQ ID NO 44
<211> LENGTH: 290
<212> TYPE: PRT
<213> ORGANISM: Artificial Sequence
<220> FEATURE:
<223> OTHER INFORMATION: Synthetic Construct

<400> SEQUENCE: 44

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Ser Gly Gly
            35                  40                  45

Gly Gly Ser Gly Gly Gly Ser Gly Gly Gly Ser Ala Glu Ser
50                  55                  60

```
Lys Tyr Gly Pro Pro Cys Pro Pro Cys Pro Ala Pro Glu Phe Leu Gly
 65                  70                  75                  80

Gly Pro Ser Val Phe Leu Phe Pro Pro Lys Pro Lys Asp Thr Leu Met
                 85                  90                  95

Ile Ser Arg Thr Pro Glu Val Thr Cys Val Val Val Asp Val Ser Gln
            100                 105                 110

Glu Asp Pro Glu Val Gln Phe Asn Trp Tyr Val Asp Gly Val Glu Val
        115                 120                 125

His Asn Ala Lys Thr Lys Pro Arg Glu Glu Gln Phe Asn Ser Thr Tyr
130                 135                 140

Arg Val Val Ser Val Leu Thr Val Leu His Gln Asp Trp Leu Asn Gly
145                 150                 155                 160

Lys Glu Tyr Lys Cys Lys Val Ser Asn Lys Gly Leu Pro Ser Ser Ile
                165                 170                 175

Glu Lys Thr Ile Ser Lys Ala Lys Gly Gln Pro Arg Glu Pro Gln Val
            180                 185                 190

Tyr Thr Leu Pro Pro Ser Gln Glu Glu Met Thr Lys Asn Gln Val Ser
        195                 200                 205

Leu Thr Cys Leu Val Lys Gly Phe Tyr Pro Ser Asp Ile Ala Val Glu
210                 215                 220

Trp Glu Ser Asn Gly Gln Pro Glu Asn Asn Tyr Lys Thr Thr Pro Pro
225                 230                 235                 240

Val Leu Asp Ser Asp Gly Ser Phe Phe Leu Tyr Ser Arg Leu Thr Val
                245                 250                 255

Asp Lys Ser Arg Trp Gln Glu Gly Asn Val Phe Ser Cys Ser Val Met
            260                 265                 270

His Glu Ala Leu His Asn His Tyr Thr Gln Lys Ser Leu Ser Leu Ser
        275                 280                 285

Leu Gly
    290

<210> SEQ ID NO 45
<211> LENGTH: 290
<212> TYPE: PRT
<213> ORGANISM: Artificial Sequence
<220> FEATURE:
<223> OTHER INFORMATION: Synthetic Construct

<400> SEQUENCE: 45

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ser Gly Gly Gly Gly Ser Gly Gly Gly Gly Ser Gly Gly
            35                  40                  45

Gly Gly Ser Gly Gly Gly Gly Ser Gly Gly Gly Gly Ser Ala Glu Ser
        50                  55                  60

Lys Tyr Gly Pro Pro Cys Pro Pro Cys Pro Ala Pro Glu Ala Ala Gly
 65                  70                  75                  80

Gly Pro Ser Val Phe Leu Phe Pro Pro Lys Pro Lys Asp Thr Leu Met
                 85                  90                  95

Ile Ser Arg Thr Pro Glu Val Thr Cys Val Val Val Asp Val Ser Gln
            100                 105                 110

Glu Asp Pro Glu Val Gln Phe Asn Trp Tyr Val Asp Gly Val Glu Val
        115                 120                 125

His Asn Ala Lys Thr Lys Pro Arg Glu Glu Gln Phe Asn Ser Thr Tyr
```

```
            130                 135                 140
Arg Val Val Ser Val Leu Thr Val Leu His Gln Asp Trp Leu Asn Gly
145                 150                 155                 160

Lys Glu Tyr Lys Cys Lys Val Ser Asn Lys Gly Leu Pro Ser Ser Ile
                165                 170                 175

Glu Lys Thr Ile Ser Lys Ala Lys Gly Gln Pro Arg Glu Pro Gln Val
                180                 185                 190

Tyr Thr Leu Pro Pro Ser Gln Glu Glu Met Thr Lys Asn Gln Val Ser
                195                 200                 205

Leu Thr Cys Leu Val Lys Gly Phe Tyr Pro Ser Asp Ile Ala Val Glu
            210                 215                 220

Trp Glu Ser Asn Gly Gln Pro Glu Asn Asn Tyr Lys Thr Thr Pro Pro
225                 230                 235                 240

Val Leu Asp Ser Asp Gly Ser Phe Phe Leu Tyr Ser Arg Leu Thr Val
                245                 250                 255

Asp Lys Ser Arg Trp Gln Glu Gly Asn Val Phe Ser Cys Ser Val Met
                260                 265                 270

His Glu Ala Leu His Asn His Tyr Thr Gln Lys Ser Leu Ser Leu Ser
            275                 280                 285

Leu Gly
    290

<210> SEQ ID NO 46
<211> LENGTH: 290
<212> TYPE: PRT
<213> ORGANISM: Artificial Sequence
<220> FEATURE:
<223> OTHER INFORMATION: Synthetic Construct

<400> SEQUENCE: 46

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ser Gly Gly Gly Gly Ser Gly Gly Gly Gly Ser Gly Gly
            35                  40                  45

Gly Gly Ser Gly Gly Gly Gly Ser Gly Gly Gly Ser Ala Glu Ser
        50                  55                  60

Lys Tyr Gly Pro Pro Cys Pro Pro Cys Pro Ala Pro Glu Phe Leu Gly
65              70                  75                  80

Gly Pro Ser Val Phe Leu Phe Pro Pro Lys Pro Lys Asp Thr Leu Met
                85                  90                  95

Ile Ser Arg Thr Pro Glu Val Thr Cys Val Val Val Asp Val Ser Gln
                100                 105                 110

Glu Asp Pro Glu Val Gln Phe Asn Trp Tyr Val Asp Gly Val Glu Val
            115                 120                 125

His Asn Ala Lys Thr Lys Pro Arg Glu Glu Gln Phe Ala Ser Thr Tyr
        130                 135                 140

Arg Val Val Ser Val Leu Thr Val Leu His Gln Asp Trp Leu Asn Gly
145                 150                 155                 160

Lys Glu Tyr Lys Cys Lys Val Ser Asn Lys Gly Leu Pro Ser Ser Ile
                165                 170                 175

Glu Lys Thr Ile Ser Lys Ala Lys Gly Gln Pro Arg Glu Pro Gln Val
                180                 185                 190

Tyr Thr Leu Pro Pro Ser Gln Glu Glu Met Thr Lys Asn Gln Val Ser
                195                 200                 205
```

```
Leu Thr Cys Leu Val Lys Gly Phe Tyr Pro Ser Asp Ile Ala Val Glu
    210                 215                 220

Trp Glu Ser Asn Gly Gln Pro Glu Asn Asn Tyr Lys Thr Thr Pro Pro
225                 230                 235                 240

Val Leu Asp Ser Asp Gly Ser Phe Phe Leu Tyr Ser Arg Leu Thr Val
                245                 250                 255

Asp Lys Ser Arg Trp Gln Glu Gly Asn Val Phe Ser Cys Ser Val Met
                260                 265                 270

His Glu Ala Leu His Asn His Tyr Thr Gln Lys Ser Leu Ser Leu Ser
            275                 280                 285

Leu Gly
    290

<210> SEQ ID NO 47
<211> LENGTH: 290
<212> TYPE: PRT
<213> ORGANISM: Artificial Sequence
<220> FEATURE:
<223> OTHER INFORMATION: Synthetic Construct

<400> SEQUENCE: 47

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ser Gly Gly Gly Gly Ser Gly Gly Gly Gly Ser Gly Gly
            35                  40                  45

Gly Gly Ser Gly Gly Gly Gly Ser Gly Gly Gly Gly Ser Ala Glu Ser
        50                  55                  60

Lys Tyr Gly Pro Pro Cys Pro Pro Cys Pro Ala Pro Glu Ala Ala Gly
65                  70                  75                  80

Gly Pro Ser Val Phe Leu Phe Pro Pro Lys Pro Lys Asp Thr Leu Met
                85                  90                  95

Ile Ser Arg Thr Pro Glu Val Thr Cys Val Val Val Asp Val Ser Gln
                100                 105                 110

Glu Asp Pro Glu Val Gln Phe Asn Trp Tyr Val Asp Gly Val Glu Val
            115                 120                 125

His Asn Ala Lys Thr Lys Pro Arg Glu Glu Gln Phe Ala Ser Thr Tyr
        130                 135                 140

Arg Val Val Ser Val Leu Thr Val Leu His Gln Asp Trp Leu Asn Gly
145                 150                 155                 160

Lys Glu Tyr Lys Cys Lys Val Ser Asn Lys Gly Leu Pro Ser Ser Ile
                165                 170                 175

Glu Lys Thr Ile Ser Lys Ala Lys Gly Gln Pro Arg Glu Pro Gln Val
            180                 185                 190

Tyr Thr Leu Pro Pro Ser Gln Glu Glu Met Thr Lys Asn Gln Val Ser
        195                 200                 205

Leu Thr Cys Leu Val Lys Gly Phe Tyr Pro Ser Asp Ile Ala Val Glu
    210                 215                 220

Trp Glu Ser Asn Gly Gln Pro Glu Asn Asn Tyr Lys Thr Thr Pro Pro
225                 230                 235                 240

Val Leu Asp Ser Asp Gly Ser Phe Phe Leu Tyr Ser Arg Leu Thr Val
                245                 250                 255

Asp Lys Ser Arg Trp Gln Glu Gly Asn Val Phe Ser Cys Ser Val Met
                260                 265                 270
```

His Glu Ala Leu His Asn His Tyr Thr Gln Lys Ser Leu Ser Leu Ser
            275                 280                 285

Leu Gly
    290

<210> SEQ ID NO 48
<211> LENGTH: 31
<212> TYPE: PRT
<213> ORGANISM: Artificial Sequence
<220> FEATURE:
<223> OTHER INFORMATION: Synthetic Construct

<400> SEQUENCE: 48

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Lys
            20                  25                  30

<210> SEQ ID NO 49
<211> LENGTH: 645
<212> TYPE: PRT
<213> ORGANISM: Artificial Sequence
<220> FEATURE:
<223> OTHER INFORMATION: Synthetic Construct

<400> SEQUENCE: 49

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg His Gly
            20                  25                  30

Glu Gly Thr Phe Thr Ser Asp Val Ser Ser Tyr Leu Glu Gly Gln Ala
        35                  40                  45

Ala Lys Glu Phe Ile Ala Trp Leu Val Lys Gly Arg Asp Ala His Lys
    50                  55                  60

Ser Glu Val Ala His Arg Phe Lys Asp Leu Gly Glu Glu Asn Phe Lys
65                  70                  75                  80

Ala Leu Val Leu Ile Ala Phe Ala Gln Tyr Leu Gln Gln Cys Pro Phe
                85                  90                  95

Glu Asp His Val Lys Leu Val Asn Glu Val Thr Glu Phe Ala Lys Thr
            100                 105                 110

Cys Val Ala Asp Glu Ser Ala Glu Asn Cys Asp Lys Ser Leu His Thr
        115                 120                 125

Leu Phe Gly Asp Lys Leu Cys Thr Val Ala Thr Leu Arg Glu Thr Tyr
    130                 135                 140

Gly Glu Met Ala Asp Cys Cys Ala Lys Gln Glu Pro Glu Arg Asn Glu
145                 150                 155                 160

Cys Phe Leu Gln His Lys Asp Asp Asn Pro Asn Leu Pro Arg Leu Val
                165                 170                 175

Arg Pro Glu Val Asp Val Met Cys Thr Ala Phe His Asp Asn Glu Glu
            180                 185                 190

Thr Phe Leu Lys Lys Tyr Leu Tyr Glu Ile Ala Arg Arg His Pro Tyr
        195                 200                 205

Phe Tyr Ala Pro Glu Leu Leu Phe Phe Ala Lys Arg Tyr Lys Ala Ala
    210                 215                 220

Phe Thr Glu Cys Cys Gln Ala Ala Asp Lys Ala Ala Cys Leu Leu Pro
225                 230                 235                 240

Lys Leu Asp Glu Leu Arg Asp Glu Gly Lys Ala Ser Ser Ala Lys Gln
                245                 250                 255

```
Arg Leu Lys Cys Ala Ser Leu Gln Lys Phe Gly Glu Arg Ala Phe Lys
            260                 265                 270

Ala Trp Ala Val Ala Arg Leu Ser Gln Arg Phe Pro Lys Ala Glu Phe
        275                 280                 285

Ala Glu Val Ser Lys Leu Val Thr Asp Leu Thr Lys Val His Thr Glu
    290                 295                 300

Cys Cys His Gly Asp Leu Leu Glu Cys Ala Asp Asp Arg Ala Asp Leu
305                 310                 315                 320

Ala Lys Tyr Ile Cys Glu Asn Gln Asp Ser Ile Ser Ser Lys Leu Lys
                325                 330                 335

Glu Cys Cys Glu Lys Pro Leu Leu Glu Lys Ser His Cys Ile Ala Glu
            340                 345                 350

Val Glu Asn Asp Glu Met Pro Ala Asp Leu Pro Ser Leu Ala Ala Asp
        355                 360                 365

Phe Val Glu Ser Lys Asp Val Cys Lys Asn Tyr Ala Glu Ala Lys Asp
    370                 375                 380

Val Phe Leu Gly Met Phe Leu Tyr Glu Tyr Ala Arg Arg His Pro Asp
385                 390                 395                 400

Tyr Ser Val Val Leu Leu Leu Arg Leu Ala Lys Thr Tyr Glu Thr Thr
                405                 410                 415

Leu Glu Lys Cys Cys Ala Ala Ala Asp Pro His Glu Cys Tyr Ala Lys
            420                 425                 430

Val Phe Asp Glu Phe Lys Pro Leu Val Glu Glu Pro Gln Asn Leu Ile
        435                 440                 445

Lys Gln Asn Cys Glu Leu Phe Glu Gln Leu Gly Glu Tyr Lys Phe Gln
    450                 455                 460

Asn Ala Leu Leu Val Arg Tyr Thr Lys Lys Val Pro Gln Val Ser Thr
465                 470                 475                 480

Pro Thr Leu Val Glu Val Ser Arg Asn Leu Gly Lys Val Gly Ser Lys
                485                 490                 495

Cys Cys Lys His Pro Glu Ala Lys Arg Met Pro Cys Ala Glu Asp Tyr
            500                 505                 510

Leu Ser Val Val Leu Asn Gln Leu Cys Val Leu His Glu Lys Thr Pro
        515                 520                 525

Val Ser Asp Arg Val Thr Lys Cys Cys Thr Glu Ser Leu Val Asn Arg
    530                 535                 540

Arg Pro Cys Phe Ser Ala Leu Glu Val Asp Glu Thr Tyr Val Pro Lys
545                 550                 555                 560

Glu Phe Asn Ala Glu Thr Phe Thr Phe His Ala Asp Ile Cys Thr Leu
                565                 570                 575

Ser Glu Lys Glu Arg Gln Ile Lys Lys Gln Thr Ala Leu Val Glu Leu
            580                 585                 590

Val Lys His Lys Pro Lys Ala Thr Lys Glu Gln Leu Lys Ala Val Met
        595                 600                 605

Asp Asp Phe Ala Ala Phe Val Glu Lys Cys Cys Lys Ala Asp Asp Lys
    610                 615                 620

Glu Thr Cys Phe Ala Glu Glu Gly Lys Lys Leu Val Ala Ala Ser Gln
625                 630                 635                 640

Ala Ala Leu Gly Leu
                645

<210> SEQ ID NO 50
<211> LENGTH: 44
<212> TYPE: PRT
<213> ORGANISM: Artificial Sequence
```

```
<220> FEATURE:
<223> OTHER INFORMATION: Synthetic Construct

<400> SEQUENCE: 50

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Lys Lys Lys Lys Lys
            35                  40

<210> SEQ ID NO 51
<211> LENGTH: 50
<212> TYPE: PRT
<213> ORGANISM: Artificial Sequence
<220> FEATURE:
<223> OTHER INFORMATION: Synthetic Construct

<400> SEQUENCE: 51

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
                20                  25                  30

Lys Asn Gly Gly Pro Ser Ser Gly Ala Pro Pro Ser Lys Lys Lys Lys
            35                  40                  45

Lys Lys
    50

<210> SEQ ID NO 52
<211> LENGTH: 38
<212> TYPE: PRT
<213> ORGANISM: Artificial Sequence
<220> FEATURE:
<223> OTHER INFORMATION: Synthetic Construct

<400> SEQUENCE: 52

His Gly Glu Gly Thr Phe Thr Ser Asp Leu Ser Lys Gln Met Glu Glu
1               5                   10                  15

Glu Ala Val Arg Leu Phe Ile Glu Trp Leu Trp Leu Lys Asn Gly Gly
                20                  25                  30

Pro Ser Ser Gly Ala Ser
            35

<210> SEQ ID NO 53
<211> LENGTH: 42
<212> TYPE: PRT
<213> ORGANISM: Artificial Sequence
<220> FEATURE:
<223> OTHER INFORMATION: Synthetic Construct

<400> SEQUENCE: 53

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
                20                  25                  30

Lys Asn Gly Gly Pro Ser Ser Gly Ala Ser
            35                  40

<210> SEQ ID NO 54
<211> LENGTH: 42
<212> TYPE: PRT
<213> ORGANISM: Artificial Sequence
<220> FEATURE:
```

```
<223> OTHER INFORMATION: Synthetic Construct

<400> SEQUENCE: 54

Asn Glu Glu Glu Glu His Gly Glu Gly Thr Phe Thr Ser Asp Leu
1               5                   10                  15

Ser Lys Gln Met Glu Glu Ala Val Arg Leu Phe Ile Glu Trp Leu
                20                  25                  30

Lys Asn Gly Gly Pro Ser Ser Gly Ala Ser
            35                  40

<210> SEQ ID NO 55
<211> LENGTH: 42
<212> TYPE: PRT
<213> ORGANISM: Artificial Sequence
<220> FEATURE:
<223> OTHER INFORMATION: Synthetic Construct

<400> SEQUENCE: 55

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Ser Lys Lys Lys Lys Lys Lys
            35                  40

<210> SEQ ID NO 56
<211> LENGTH: 48
<212> TYPE: PRT
<213> ORGANISM: Artificial Sequence
<220> FEATURE:
<223> OTHER INFORMATION: Synthetic Construct

<400> SEQUENCE: 56

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
                20                  25                  30

Lys Asn Gly Gly Pro Ser Ser Gly Ala Ser Lys Lys Lys Lys Lys
            35                  40                  45

<210> SEQ ID NO 57
<211> LENGTH: 48
<212> TYPE: PRT
<213> ORGANISM: Artificial Sequence
<220> FEATURE:
<223> OTHER INFORMATION: Synthetic Construct

<400> SEQUENCE: 57

Asp Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
                20                  25                  30

Lys Asn Gly Gly Pro Ser Ser Gly Ala Ser Lys Lys Lys Lys Lys
            35                  40                  45
```

CO-ADMINISTRATION OF FGF-21 AND GLP-1 TO TREAT DIABETES AND LOWER BLOOD GLUCOSE

This application is a continuation of U.S. application Ser. No. 12/668,475, filed Jan. 11, 2010, which is a National Phase Application under 35 U.S.C. 371 of PCT Application No. PCT/US2008/071508, filed Jul. 30, 2008, which claims the priority of U.S. Provisional Application No. 60/953,785, filed Aug. 3, 2007.

The present invention relates to compositions that comprise an FGF-21 compound and a GLP-1 compound. These compositions can be used to lower body weight and treat obesity.

BACKGROUND OF THE INVENTION

Obesity, and especially upper body obesity, is the most common nutritional disorder in the over-nourished populations of the world. Current methods for promoting weight loss are not completely satisfactory. Unfortunately, an estimated 33 billion dollars a year are spent on weight-loss measures that are largely futile. Thus, new methods and compositions such as pharmaceutical agents that promote weight-loss are urgently needed to complement old approaches.

Fibroblast growth factor 21 (FGF-21) belongs to a family of large polypeptides widely expressed in developing and adult tissues that play crucial roles in multiple physiological functions. FGF-21 has been reported to stimulate glucose-uptake in mouse adipocytes after prolonged treatment, in the presence and absence of insulin, and to decrease fed and fasting blood glucose, triglycerides, and glucagon levels in ob/ob and db/db mice in a dose-dependent manner, thus, providing the basis for the use of FGF-21 as a therapy for treating diabetes and obesity (WO03/011213).

In addition to its beneficial effects on Type 2 diabetes, Glucagon-like peptide-1 (GLP-1) compounds have been described for the treatment of obesity, (WO98/019698). Although both FGF-21 and GLP-1 compounds have shown positive effects in treating obesity, there has not been any indication that a combination of FGF-21 compounds and GLP-1 compounds would provide a synergistic effect on lowering body weight. There is thus, still a need for additional beneficial therapeutics for weight loss.

Applicants have determined that a combination of an FGF-21 compound and a GLP-1 compound have an unexpected synergistic effect on lowering body weight.

SUMMARY OF THE INVENTION

The present invention relates to compositions comprising a FGF-21 compound and a GLP-1 compound. The present invention also provides a method of lowering body weight comprising administering an FGF-21 compound in combination with a GLP-1 compound. In another embodiment, the present invention provides a method of treating obesity comprising administering a FGF-21 compound in combination with a GLP-1 compound.

The present invention also provides compositions comprising a FGF-21 compound and an exendin compound. The present invention also provides a method of lowering body weight comprising administering an FGF-21 compound in combination with an exendin compound. In another embodiment, the present invention provides a method of treating obesity comprising administering a FGF-21 compound in combination with an exendin compound.

DETAILED DESCRIPTION

A "FGF-21 compound" is defined as a compound comprising native human FGF-21 (SEQ ID NO: 2), an FGF-21 analog, or an FGF-21 derivative. The FGF-21 compounds of the present invention retain FGF-21 activity as measured in assays as described in Kharitonenkov, et al., (Journal of Clinical Investigation, 115(6):1627 (2005)).

A "FGF-21 analog" is defined as a molecule having a modification including one or more amino acid substitutions, deletions, inversions or additions when compared with SEQ ID NO: 2.

A "FGF-21 derivative" is defined as a molecule having the amino acid sequence of human FGF-21 (SEQ ID NO: 2) or of a FGF-21 analog but additionally having at least one chemical modification of one or more of its amino acid side groups, $\alpha$-carbon atoms, terminal amino group, or terminal carboxylic acid group. Modifications at amino acid side groups include acylation of lysine e-amino groups, N-alkylation of arginine, histidine, or lysine, alkylation of glutamic or aspartic carboxylic acid groups, and deamidation of glutamine or asparagine. Modifications of the terminal amino include the des-amino, N-lower alkyl, N-di-lower alkyl, and N-acyl modifications. Modifications of the terminal carboxy group include the amide, lower alkyl amide, dialkyl amide, and lower alkyl ester modifications. A lower alkyl is a $C_1$-$C_4$ alkyl. Furthermore, one or more side groups, or terminal groups, may be protected by protective groups known to the ordinarily-skilled protein chemist. The $\alpha$-carbon of an amino acid may be mono- or di-methylated. The chemical modification may also include "pegylation."

Specific substitutions to human FGF-21, FGF-21 analog or FGF-21 derivative indicated using the specific amino acid present after substitution or modification at a particular residue followed by the residue number. For example, $Cys^{118}$-FGF-21 indicates that there has been a cysteine introduced at position 118 of human FGF-21.

A "GLP-1 compound" is defined as a compound comprising the amino acid sequence of native human GLP-1 (SEQ ID NO: 3), a GLP-1 analog or GLP-1 derivative, which maintains GLP-1 activity. GLP-1 activity may be measured by methods known in the art, including using in vivo experiments and in vitro assays that measure GLP-1 receptor binding activity or receptor activation, e.g., assays employing pancreatic islet cells or insulinoma cells, as described in EP 619,322, Gelfand, et al., and U.S. Pat. No. 5,120,712, respectively. GLP-1 compounds are well known in the art. See, e.g. PCT International Application Publication Nos. WO 03/040309, U.S. Pat. Nos. 6,593,295, 7,141,547, and 7,176,278.

A "GLP-1 analog" is defined as a molecule having a modification including one or more amino acid substitutions, deletions, inversions, or additions when compared with SEQ ID NO: 3. "GLP-1 analog" also includes "GLP-1 fusion proteins" where the GLP-1 fusion protein is a heterologous protein comprising a GLP-1 or GLP-1 analog and a second polypeptide selected from the group consisting of human albumin, human albumin analogs, fragments of human albumin, transferrin, transferrin analogs, transferrin derivatives, fragments of transferring, the Fc portion of an immunoglobulin, an analog of the Fc portion of an immunoglobulin, and fragments of the Fc portion of an immunoglobulin, and wherein the C-terminus of the first polypeptide is fused to the N-terminus of the second polypeptide. The GLP-1 or GLP-1 analog may be fused to the second polypeptide via a peptide linker. The GLP-1 fusion proteins of the present invention contain an Fc portion which is derived from human IgG4 but comprises one or more substitutions compared to the wild-type human sequence (SEQ ID NO: 5).

A "GLP-1 derivative" is defined as a molecule having the amino acid sequence of native human GLP-1 or of a GLP-1 analog, but additionally having at least one chemical modification of one or more of its amino acid side groups, a-carbon atoms, terminal amino group, or terminal carboxylic acid group. Modifications at amino acid side groups include acylation of lysine e-amino groups, N-alkylation of arginine, histidine, or lysine, alkylation of glutamic or aspartic carboxylic acid groups, and deamidation of glutamine or asparagine. Modifications of the terminal amino include the desamino, N-lower alkyl, N-di-lower alkyl, and N-acyl modifications. Modifications of the terminal carboxy group include the amide, lower alkyl amide, dialkyl amide, and lower alkyl ester modifications. A lower alkyl is a $C_1$-$C_4$alkyl. Furthermore, one or more side groups, or terminal groups, may be protected by protective groups known to the ordinarily-skilled protein chemist. The α-carbon of an amino acid may be mono- or di-methylated. The chemical modification may also include the pegylation of an amino acid of the peptide or polypeptide.

The nomenclature used herein to refer to specific GLP-1 analogs and GLP-1 derivatives is defined as follows: Specific substitutions to a GLP-1 analog and GLP-1 derivative are indicated using the specific amino acid being substituted followed by the residue number. GLP-1 (7-37) indicates that the GLP-1 analog portion of the mature fusion protein begins with His at position 7 and ends with Gly at position 37. In the case of additions of amino acids to a GLP-1 amino acid sequence, the added amino acid is indicated followed by the position at which it is present. For example, the addition of two serine residues to the C-terminus of wild type GLP-1 will be referred to as $Ser^{38}$-$Ser^{39}$-GLP-1.

An "exendin compound" is defined as a compound comprising the amino acid sequence of exendin-4 (SEQ ID NO: 4), an exendin-4 analog or exendin-4 derivative, wherein the exendin compound maintains exendin-4 activity.

An "exendin-4 analog" is defined as a compound having a modification including one or more amino acid substitutions, deletions, inversions, or additions when compared with the amino acid sequence of exendin-4 (SEQ ID NO: 4). "Exendin-4 analog" also includes "exendin fusion proteins" where the "exendin fusion protein" is a heterologous protein comprising an exendin-4 or exendin-4 analog and a second polypeptide selected from the group consisting of human albumin, human albumin analogs, fragments of human albumin, transferrin, transferrin analogs, transferrin derivatives, fragments of transferring, the Fc portion of an immunoglobulin, an analog of the Fc portion of an immunoglobulin, and fragments of the Fc portion of an immunoglobulin, and wherein the C-terminus of the first polypeptide is fused to the N-terminus of the second polypeptide. The exendin-4 or exendin-4 analog may be fused to the second polypeptide via a peptide linker. The exendin-4 fusion proteins of the present invention may contain an Fc portion which is derived from human IgG4 comprises one or more substitutions compared to the wild-type human sequence (SEQ ID NO: 5).

An "exendin-4 derivative" is defined as a compound having the amino acid sequence of exendin-4 or of an exendin-4 analog, but additionally having at least one chemical modification of one or more of its amino acid side groups, a-carbon atoms, terminal amino group, or terminal carboxylic acid group. Modifications at amino acid side groups include acylation of lysine e-amino groups, N-alkylation of arginine, histidine, or lysine, alkylation of glutamic or aspartic carboxylic acid groups, and deamidation of glutamine or asparagine. Modifications of the terminal amino include the desamino, N-lower alkyl, N-di-lower alkyl, and N-acyl modifications. Modifications of the terminal carboxy group include the amide, lower alkyl amide, dialkyl amide, and lower alkyl ester modifications. A lower alkyl is a $C_1$-$C_4$alkyl. Furthermore, one or more side groups, or terminal groups, may be protected by protective groups known to the ordinarily-skilled protein chemist. The α-carbon of an amino acid may be mono- or di-methylated. The chemical modification may also include pegylation.

As used herein, the Fc portion of an immunoglobulin has the meaning commonly given to the term in the field of immunology. Specifically, this term refers to an antibody fragment which does not contain the two antigen binding regions (the Fab fragments) from the antibody. The Fc portion consists of the constant region of an antibody from both heavy chains, which associate through non-covalent interactions and disulfide bonds. The Fc portion can include the hinge regions and extend through the CH2 and CH3 domains to the c-terminus of the antibody. The Fc portion can further include one or more glycosylation sites.

The fusion proteins described herein may also contain a linker ("L"). The linker may comprise the sequence Gly-Gly-Gly-Gly-Ser-Gly-Gly-Gly-Gly-Ser-Gly-Gly-Gly-Gly-Ser (SEQ ID NO: 6). The number immediately preceding the L refers to the number of linkers separating the particular peptide or protein portion from the Fc portion. A linker specified as 1.5L refers to the sequence Gly-Ser-Gly-Gly-Gly-Gly-Ser-Gly-Gly-Gly-Gly-Ser-Gly-Gly-Gly-Gly-Ser-Gly-Gly-Gly-Gly-Ser (SEQ ID NO: 7). IgG4 refers to an analog of the human IgG4 Fc sequence specified as SEQ ID NO: 5. Substitutions in the IgG4 Fc portion of the fusion protein are indicated in parenthesis. The wild-type amino acid is specified by its common abbreviation followed by the position number in the context of the entire IgG4 sequence using the EU numbering system followed by the amino acid being substituted at that position specified by its common abbreviation.

"Pegylation" or "Pegylated" refers to a compound of the present invention that is chemically modified by covalent attachment of a molecule or molecules of polyethylene glycol or a derivative thereof. Furthermore, it is intended that the term "PEG" refers to polyethylene glycol or a derivative thereof as are known in the art. In its typical form, PEG is a linear polymer with terminal hydroxyl groups and has the formula HO—$CH_2CH_2$—($CH_2CH_2O$)n-$CH_2CH_2$—OH, where n is from about 8 to about 4000. The terminal hydrogen may be substituted with a protective group such as an alkyl or aryl group. Preferably, PEG has at least one hydroxy group, more preferably it is a terminal hydroxy group. It is this hydroxy group which is preferably activated to react with the peptide. There are many forms of PEG useful for the present invention. Numerous derivatives of PEG exist in the art and are suitable for use in the invention. The PEG molecule covalently attached to compounds in the present invention is not intended to be limited to a particular type PEG's molecular weight is preferably from 500-100,000 daltons and more preferably from 20,000-60,000 daltons and most preferably from 20,000-40,000 daltons. PEG may be linear or branched.

"In combination with" or "coadministration" refers to the administration of a FGF-21 compound with a GLP-1 compound either simultaneously, sequentially or a combination thereof. The combination therapy of a FGF-21 compound with a GLP-1 compound results in a synergistic effect in lowering body weight and thus, in the treatment of obesity.

The combination therapy also results in a synergistic effect on lower elevated blood glucose levels and thus, a potential use in the treatment of diabetes.

The term "synergy" or "synergistic" as used herein is defined to mean a combination of components wherein the effect of the combination is greater than the additive individual effects of each component of the combination. For purposes of the present invention, "effect" refers to a loss in body weight, lowering of body weight or a reduction in blood glucose levels.

The FGF-21 compounds, the GLP-1 compounds and the exendin compounds of the present invention may be made using various techniques known to one of skill in the art. For example, the FGF-21, GLP-1 and exendin compounds may be made using recombinant techniques. As the DNA sequences of mature human FGF-21 (SEQ ID NO: 1), native GLP-1, and exendin-4 are known, PCR methodology may be used to isolate genes encoding the corresponding gene. Further, one of skill in the art is aware of various methods to introduce changes in the DNA sequence so as to effect desired changes in the amino acid sequence of the resulting FGF-21, GLP-1 or exendin compounds.

The GLP-1 and the exendin peptides of the present invention can also be prepared by using standard methods of solid-phase peptide synthesis techniques. Peptide synthesizers are commercially available from, for example, Applied Biosystems in Foster City, Calif. Reagents for solid phase synthesis are commercially available, for example, from Midwest Biotech (Fishers, Ind.). Solid phase peptide synthesizers can be used according to manufacturer's instructions for blocking interfering groups, protecting the amino acid to be reacted, coupling, decoupling, and capping of unreacted amino acids.

A wide variety of methods have been described in the art to covalently conjugate PEGs to peptides (for review article see, Roberts, M. et al. *Advanced Drug Delivery Reviews*, 54:459-476, 2002). Pegylation of peptides at the carboxy-terminus may be performed via enzymatic coupling using recombinant compounds of the present invention as a precursor or alternative methods known in the art and described. See e.g. U.S. Pat. No. 4,343,898 or *International Journal of Peptide & Protein Research.* 43:127-38, 1994.

Various methods of protein purification may be employed and such methods are known in the art and described, for example, in Deutscher, *Methods in Enzymology* 182: 83-9 (1990) and Scopes, *Protein Purification: Principles and Practice*, Springer-Verlag, NY (1982). The purification step(s) selected will depend on the nature of the production process used and the particular protein produced. For example, fusion proteins comprising an Fc fragment can be effectively purified using a Protein A or Protein G affinity matrix. Low or high pH buffers can be used to elute the fusion protein from the affinity matrix. Mild elution conditions will aid in preventing irreversible denaturation of the fusion protein.

Coadministration of FGF-21 compounds, GLP-1 compounds and exendin compounds of the present invention may be via any route known to be effective by the physician of ordinary skill. Peripheral parenteral is one such method. Parenteral administration is commonly understood in the medical literature as the injection of a dosage form into the body by a sterile syringe or some other mechanical device such as an infusion pump. Peripheral parenteral routes can include intravenous, intramuscular, subcutaneous, and intraperitoneal routes of administration.

Those skilled in the art can readily optimize pharmaceutically effective dosages and administration regimens for the combinations of the present invention, as determined by good medical practice and the clinical condition of the individual patient. For example, a typical dose range for the FGF-21 compounds of the present invention will range from about 0.01 mg per day to about 1000 mg per day for an adult. A typical dose range for the GLP-1 derivative compounds of the present invention will range from about 0.01 mg per day to about 1000 mg per day for an adult. For GLP-1 fusion proteins, doses may be in the range of 0.01 to 1 mg/kg body weight, preferably in the range of 0.05 to 0.5 mg/kg body weight.

In an embodiment, the present invention provides a composition comprising a FGF-21 compound and a GLP-1 compound. In another embodiment, the present invention provides a composition comprising a FGF-21 compound and a GLP-1 compound, wherein the FGF-21 compound is selected from the group consisting of human FGF-21, an FGF-21 analog and an FGF-21 derivative and wherein the GLP-1 compound is selected from the group consisting of GLP-1 analog, GLP-1 derivative and GLP-1 fusion proteins. In a preferred embodiment, the composition comprises an FGF-21 analog and a GLP-1 analog. In another preferred embodiment, the composition comprises a FGF-21 analog and a GLP-1 derivative. In another preferred embodiment, the composition comprises a FGF-21 analog and a GLP-1 fusion protein.

In another embodiment, the present invention provides a composition comprising an FGF-21 compound and an exendin compound. In a preferred embodiment, the composition comprises a FGF-21 compound and an exendin compound, wherein the FGF-21 compound is selected from the group consisting of human FGF-21, an FGF-21 analog and an FGF-21 derivative and wherein the exendin compound is selected from the group consisting of exendin-4, an exendin-4 analog, an exendin-4 derivative, and an exendin-4 agonist. In a preferred embodiment, the composition comprises a FGF-21 analog and exendin-4. In another preferred embodiment, the composition comprises a FGF-21 analog and an exendin-4 analog. In another preferred embodiment, the composition comprises a FGF-21 analog and an exendin-4 derivative. In another preferred embodiment, the composition comprises a FGF-21 analog and an exendin-4 agonist.

The present invention also provides a method of lowering body weight comprising administering a FGF-21 compound in combination with a GLP-1 compound. In a more preferred embodiment, administering a FGF-21 compound in combination with a GLP-1 compound results in a synergistic effect on weight loss. In another embodiment, the method of lowering body weight comprises administering a FGF-21 compound in combination with a GLP-1 compound, wherein the FGF-21 compound is selected from the group consisting of human FGF-21, an FGF-21 analog and an FGF-21 derivative and wherein the GLP-1 compound is selected from the group consisting of GLP-1 analog, GLP-1 derivative and GLP-1 fusion protein. In a preferred embodiment, the method of lowering body weight comprises administering a FGF-21 analog in combination with a GLP-1 analog. In another preferred embodiment, the method of lowering body weight comprises administering a FGF-21 analog in combination with a GLP-1 derivative. In another preferred embodiment, the method of lowering body weight comprises administering a FGF-21 analog and a GLP-1 fusion protein.

The present invention also provides a method of lowering body weight comprising administering a FGF-21 compound in combination with an exendin compound. In more preferred embodiment, administering a FGF-21 compound in combination with an exendin compound results in a synergistic effect on weight loss. In an embodiment, the method of lowering body weight comprises administering a FGF-21 compound in combination with an exendin compound, wherein the FGF-21 compound is selected from the group consisting of human FGF-21, an FGF-21 analog and an FGF-21 derivative and wherein the exendin compound is selected from the group consisting of exendin-4, an exendin-4 analog, an exendin-4 derivative, and an exendin-4 agonist. In a preferred embodiment, the method of lowering body weight comprises administering a FGF-21 analog in combination with exendin-4. In another preferred embodiment, the method of lowering body weight comprises administering a FGF-21 analog in combination with an exendin-4 analog. In another preferred embodiment, the method of lowering body weight comprises administering a FGF-21 analog and an exendin-4 derivative. In another preferred embodiment, the method of lowering body weight comprises administering a FGF-21 analog and an exendin-4 agonist.

The present invention also provides a method of treating obesity comprising administering a FGF-21 compound in combination with a GLP-1 compound. In more preferred embodiment, administering a FGF-21 compound in combination with a GLP-1 compound results in a synergistic effect on weight loss. In an embodiment, the method of treating obesity comprises administering a FGF-21 compound in combination with a GLP-1 compound, wherein the FGF-21 compound is selected from the group consisting of human FGF-21, an FGF-21 analog and an FGF-21 derivative and wherein the GLP-1 compound is selected from the group consisting of GLP-1 analog, GLP-1 derivative and GLP-1 fusion protein. In a preferred embodiment, the method of treating obesity comprises administering a FGF-21 analog in combination with a GLP-1 analog. In another preferred embodiment, the method of treating obesity comprises administering a FGF-21 analog in combination with a GLP-1 derivative. In another preferred embodiment, the method of treating obesity comprises administering a FGF-21 analog and a GLP-1 fusion protein.

The present invention also provides a method of treating obesity comprising administering a FGF-21 compound in combination with an exendin compound. In more preferred embodiment, administering a FGF-21 compound in combination1 with an exendin compound results in a synergistic effect on weight loss. In an embodiment, the method of treating obesity comprises administering a FGF-21 compound in combination with an exendin compound, wherein the FGF-21 compound is selected from the group consisting of human FGF-21, an FGF-21 analog and an FGF-21 derivative and wherein the exendin compound is selected from the group consisting of exendin-4, an exendin-4 analog, an exendin-4 derivative, and exendin-4 agonist. In a preferred embodiment, the method of treating obesity comprises administering a FGF-21 analog in combination with exendin-4. In another preferred embodiment, the method of treating obesity comprises administering a FGF-21 analog in combination with an exendin-4 analog. In another preferred embodiment, the method of treating obesity comprises administering a FGF-21 analog and an exendin-4 derivative. In another preferred embodiment, the method of treating obesity comprises administering a FGF-21 analog and an exendin-4 agonist.

The present invention also provides for the use of a FGF-21 compound and a GLP-1 compound in the manufacture of a medicament to lower body weight. The present invention also provides for the use of a FGF-21 compound and a GLP-1 compound in the manufacture of a medicament to lower body weight, wherein the FGF-21 compound is selected from the group consisting of human FGF-21, an FGF-21 analog and an FGF-21 derivative and wherein the GLP-1 compound is selected from the group consisting of a GLP-1 analog, a GLP-1 derivative and a GLP-1 fusion protein. In a preferred embodiment, the present invention provides for the use of a FGF-21 analog and a GLP-1 analog in the manufacture of a medicament to lower body weight. In another preferred embodiment, the present invention provides for the use of a FGF-21 analog and a GLP-1 derivative in the manufacture of a medicament to lower body weight. In another preferred embodiment, the present invention provides for the use of a FGF-21 analog and a GLP-1 fusion protein in the manufacture of a medicament to lower body weight.

The present invention also provides for the use of a FGF-21 compound and an exendin compound in the manufacture of a medicament to lower body weight. The present invention also provides for the use of a FGF-21 compound and an exendin compound in the manufacture of a medicament to lower body weight, wherein the FGF-21 compound is selected from the group consisting of human FGF-21, an FGF-21 analog and an FGF-21 derivative and wherein the exendin compound is selected from the group consisting of exendin-4, an exendin-4 analog, an exendin-4 derivative, and an exendin-4 agonist. In a preferred embodiment, the present invention provides for the use of a FGF-21 analog and an exendin-4 analog in the manufacture of a medicament to lower body weight. In another preferred embodiment, the present invention provides for the use of a FGF-21 analog and an exendin-4 derivative in the manufacture of a medicament to lower body weight. In another preferred embodiment, the present invention provides for the use of a FGF-21 analog and an exendin-4 agonist in the manufacture of a medicament to lower body weight.

The present invention also provides for the use of a FGF-21 compound and a GLP-1 compound in the manufacture of a medicament for the treatment of obesity. The present invention also provides for the use of a FGF-21 compound and a GLP-1 compound in the manufacture of a medicament for the treatment of obesity, wherein the FGF-21 compound is selected from the group consisting of human FGF-21, FGF-21 analog and an FGF-21 derivative and wherein the GLP-1 compound is selected from the group consisting of a GLP-1 analog, a GLP-1 derivative and a GLP-1 fusion protein. In a preferred embodiment, the present invention provides for the use of a FGF-21 analog and GLP-1 analog in the manufacture of a medicament for the treatment of obesity. In another preferred embodiment, the present invention provides for the use of a FGF-21 analog and a GLP-1 derivative in the manufacture of a medicament for the treatment of obesity. In another preferred embodiment, the present invention provides for the use of a FGF-21 analog and a GLP-1 fusion protein in the manufacture of a medicament for the treatment of obesity.

The present invention also provides for the use of a FGF-21 compound and an exendin compound in the manufacture of a medicament to treat obesity. The present invention also provides for the use of a FGF-21 compound and an exendin compound in the manufacture of a medicament to lower body weight, wherein the FGF-21 compound is selected from the group consisting of human FGF-21, FGF-21 analog and an FGF-21 derivative and wherein the exendin compound is selected from the group consisting of exendin-4, exendin-4 analog, an exendin-4 derivative, and an exendin-4 agonist. In a preferred embodiment, the present invention provides for the use of a FGF-21 analog and an exendin-4 analog in the manufacture of a medicament to treat obesity. In another preferred embodiment, the present invention provides for the use of a FGF-21 analog and an exendin-4 derivative in the manufacture of a medicament to treat obesity. In another preferred embodiment, the present invention provides for the use of a FGF-21 analog and an exendin-4 agonist in the manufacture of a medicament to treat obesity.

The FGF-21 compounds of the present invention may be human FGF-21, a FGF-21 analog or a FGF-21 derivative. In a preferred embodiment, the FGF-21 compound of the present invention is a FGF-21 analog. In a more preferred embodiment, the present invention provides FGF-21 compounds comprising one or two engineered disulfide bonds. In a more preferred embodiment, the present invention provides FGF-21 compounds which comprise an amino acid sequence comprising a cysteine substitution at positions 21, 26, 33, 118, 119, 121, 122, or 134 of FGF-21 (SEQ ID NO: 2). In another preferred embodiment, the FGF-21 compound comprises an amino acid sequence comprising an amino acid substitution at position 167 of FGF-21 (SEQ ID NO: 2), wherein the substitution is not Ser or Tyr. In another preferred embodiment, the FGF-21 compound comprises an amino acid sequence comprising an amino acid substitution at position 121 of FGF-21 (SEQ ID NO: 2), wherein the substitution is any amino acid except Gln or Asn. In a more preferred embodiment, the amino acid at position 121 of FGF-21 (SEQ ID NO: 2) is selected from the group consisting of Ala, Val, Ser, Asp, or Glu. In a more preferred embodiment, the FGF-21 compound comprises an amino acid sequence selected from the group consisting of $Cys^{118}$-$Cys^{134}$-FGF-21 (SEQ ID NO: 9), $Cys^{118}$-$Cys^{134}$-$Ala^{167}$-FGF-21 (SEQ ID NO: 10), $Cys^{21}$-$Cys^{33}$-$Ala^{167}$-FGF-21 (SEQ ID NO: 11), $Cys^{26}$-$Cys^{122}$-$Ala^{167}$-FGF-21 (SEQ ID NO: 12), and $Cys^{118}$-$Cys^{134}$-$Ala^{121}$-$Ala^{167}$-FGF-21 (SEQ ID NO: 13). In a more preferred embodiment, the FGF-21 compound consists of an amino acid sequence selected from the group consisting of $Cys^{118}$-$Cys^{134}$-FGF-21 (SEQ ID NO: 9), $Cys^{118}$-$Cys^{134}$-$Ala^{167}$-FGF-21 (SEQ ID NO: 10), $Cys^{21}$-$Cys^{33}$-$Ala^{167}$-FGF-21 (SEQ ID NO: 11), $Cys^{26}$-$Cys^{122}$-$Ala^{167}$-FGF-21 (SEQ ID NO: 12), and $Cys^{118}$-$Cys^{134}$-$Ala^{121}$-$Ala^{167}$-FGF-21 (SEQ ID NO:13).

In an embodiment, the present invention provides FGF-21 compounds which consist of a cysteine substitution at positions 21, 26, 33, 118, 119, 121, 122, or 134 of FGF-21 (SEQ ID NO: 2). In another embodiment, the FGF-21 compound consist of an amino acid substitution at position 167 of FGF-21 (SEQ ID NO: 2), wherein the substitution is not Ser or Tyr. In another preferred embodiment, the FGF-21 compound consists of a substitution at position 121 of FGF-21 (SEQ ID NO: 2), wherein the substitution is any amino acid except Gln or Asn. In a more preferred embodiment, the amino acid at position 121 of FGF-21 (SEQ ID NO: 2) is selected from the group consisting of Ala, Val, Ser, Asp, or Glu. In a more preferred embodiment, the FGF-21 compound consists of an amino acid sequence selected from the group consisting of $Cys^{118}$-$Cys^{134}$-FGF-21 (SEQ ID NO: 9), $Cys^{118}$-$Cys^{134}$-$Ala^{167}$-FGF-21 SEQ ID NO: 10), $Cys^{21}$-$Cys^{33}$-$Ala^{167}$-FGF-21 (SEQ ID NO:11), $Cys^{26}$-$Cys^{122}$-$Ala^{167}$-FGF-21 (SEQ ID NO: 12), and $Cys^{118}$-$Cys^{134}$-$Ala^{121}$-$Ala^{167}$-FGF-21 (SEQ ID NO:13).

Further, the present invention provides GLP-1 compounds to be used in combination with the FGF-21 compounds of the present invention. In an embodiment, the GLP-1 compound is a GLP-1 analog, GLP-1 derivative, or a GLP-1 fusion protein. In a more preferred embodiment, the GLP-1 compound is a GLP-1 analog or derivative. In a preferred embodiment, the GLP-1 compound is a GLP-1 analog. In a more preferred embodiment, the GLP-1 compound comprises of an amino acid sequence of SEQ ID NO: 14

```
His Xaa Glu Gly Thr Phe Thr Ser Asp Val Ser Ser
        10                      15

Tyr Leu Glu Xaa Gln Ala Ala Lys Glu Phe Ile Ala
        20              25                      30

Trp Leu Xaa Xaa Gly Xaa Xaa Xaa Xaa Xaa Xaa
                35                  40

Xaa Xaa Xaa
        45
``` wherein

Xaa at position 8 is Gly, Ala, Val,
Xaa at position 22 is Gly, Glu, Asp, or Lys,
Xaa at position 33 is Val, or Ile,
Xaa at position 34 is Lys or Arg,
Xaa at position 36 is Arg or Gly,
Xaa at position 37 is selected from the group consisting of $NH_2$, Gly and Pro,
Xaa at position 38 is Ser or absent,
Xaa at position 39 is Ser or absent,
Xaa at position 40 is Gly or absent,
Xaa at position 41 is Ala or absent,
Xaa at position 42 is Pro or absent,
Xaa at position 43 is Pro or absent,
Xaa at position 44 is Pro or absent, and
Xaa at position 45 is Ser or absent.

In an embodiment, the GLP-1 compound comprises Ala at $Xaa_8$. In another embodiment, the GLP-1 compound comprises Val at $Xaa_8$. In another embodiment, the GLP-1 compound comprises Gly at $Xaa_{22}$. In a preferred embodiment, the GLP-1 compound comprises Gly at $Xaa_{22}$. In a preferred embodiment, the GLP-1 compound comprises Lys at $Xaa_{34}$. In another preferred embodiment, the GLP-1 compound comprises Arg at $Xaa_{34}$. In a more preferred embodiment, the amino acid sequence of the GLP-1 analog comprises $Val^8$-$Glu^{22}$-$Ile^{33}$-$Gly^{36}$-$Pro^{37}$-$Ser^{38}$-$Ser^{39}$-$Gly^{40}$-$Ala^{41}$-$Pro^{43}$-$Pro^{44}$-$Ser^{45}$-GLP-1 (SEQ ID NO: 19). In another embodiment, the amino acid sequence of the GLP-1 analog consists of $Val^8$-$Glu^{22}$-$Ile^{33}$-$Gly^{36}$-$Pro^{37}$-$Ser^{38}$-$Ser^{39}$-$Gly^{40}$-$Ala^{41}$-$Pro^{42}$-$Pro^{43}$-$Pro^{44}$-$Ser^{45}$-GLP-1 (SEQ ID NO: 19).

In a preferred embodiment, the amino acid sequence of the GLP-1 compound comprises $Val^8$-GLP-1 (SEQ ID NO: 15). In a preferred embodiment, the amino acid sequence of the GLP-1 compound consists of the amino acid sequence $Val^8$-GLP-1 (SEQ ID NO: 15). In another preferred embodiment, the amino acid sequence of the GLP-1 compound comprises $Arg^{34}$-GLP-1 (SEQ ID NO: 16). In another preferred embodiment, the amino acid sequence of the GLP-1 compound consists of $Arg^{34}$-GLP-1 (SEQ ID NO: 16). In another preferred embodiment, the amino acid sequence of the GLP-1 compound comprises $Val^8$-$Glu^{22}$-GLP-1 (SEQ ID NO: 17). In another preferred embodiment, the amino acid sequence of the GLP-1 compound consists of $Val^8$-$Glu^{22}$-GLP-1 (SEQ ID NO: 17). In another preferred embodiment, the amino acid sequence of $Val^8$-$Glu^{22}$-GLP-1 (SEQ ID NO: 17) comprises of five additional amino acid sequence substitutions. In another preferred embodiment, the amino acid sequence of $Val^8$-$Glu^{22}$-GLP-1 (SEQ ID NO: 17) consists of five additional amino acid sequence substitutions. In another preferred embodiment, the amino acid sequence of $Val^8$-$Glu^{22}$-GLP-1 (SEQ ID NO: 17) comprises of four additional amino acid sequence substitutions. In another preferred embodiment, the amino acid sequence of $Val^8$-$Glu^{22}$-GLP-1 (SEQ ID NO: 17) consists of four additional amino acid sequence substitutions. In another preferred embodiment, the amino acid sequence of $Val^8$-$Glu^{22}$-GLP-1 (SEQ ID NO: 17) comprises of three additional amino acid sequence substitutions. In another preferred embodiment, the amino acid sequence of Val$^8$-Glu$^{22}$-GLP-1 (SEQ ID NO: 17) consists of three additional amino acid sequence substitutions. In another preferred embodiment, the amino acid sequence of Val$^8$-Glu$^{22}$-GLP-1 (SEQ ID NO: 17) comprises of two additional amino acid sequence substitutions. In another preferred embodiment, the amino acid sequence of Val$^8$-Glu$^{22}$-GLP-1 (SEQ ID NO: 17) consists of two additional amino acid sequence substitutions. In another preferred embodiment, the amino acid sequence of Val$^8$-Glu$^{22}$-GLP-1 (SEQ ID NO: 17) comprises of one additional amino acid sequence substitution. In another preferred embodiment, the amino acid sequence of Val$^8$-Glu$^{22}$-GLP-1 (SEQ ID NO: 17) consists of one additional amino acid sequence substitution.

The present invention also provides GLP-1 derivatives in combination with FGF-21 compounds. In another preferred embodiment, the GLP-1 derivative is pegylated. In a preferred embodiment, the GLP-1 derivative comprises of an amino acid sequence of SEQ ID NO: 20

```
His Xaa Glu Gly Thr Phe Thr Ser Asp Val Ser Ser
        10                      15
Tyr Leu Glu Xaa Gln Ala Ala Lys Glu Phe Ile Ala
    20                  25                  30
Trp Leu Xaa Lys Gly Gly Pro Ser Ser Gly Ala Pro
            35                      40
Pro Pro Cys Xaa
            45
``` wherein
Xaa at position 8 is: D-Ala, Gly, Val, Leu, Ile, Ser, or Thr;
Xaa at position 22 is: Gly, Glu, Asp, or Lys;
Xaa at position 33 is: Val or Ile
Xaa at position 46 is: Cys or Cys-NH$_2$
and wherein one PEG molecule is covalently attached to Cys$^{45}$ and one PEG molecule is covalently attached to Cys$^{46}$ or Cys$^{46}$-NH$_2$. In another embodiment, the GLP-1 derivative consists of the amino acid sequence of SEQ ID NO:20.

In an embodiment, Xaa$_8$ is Val or Gly. In another embodiment, Xaa$_{22}$ is Gly or Glu. In another embodiment, Xaa$_{33}$ is Ile. In an embodiment, Xaa$_{46}$ is Cys-NH$_2$. In a preferred embodiment, the GLP-1 derivative comprises of the amino acid sequence of Val$^8$-Glu$^{22}$-Ile$^{33}$-Cys-NH$_2$$^{46}$-GLP-1 (SEQ ID NO: 21). In a preferred embodiment, the GLP-1 derivative consists of the amino acid sequence of Val$^8$-Gly$^{22}$-Ile$^{33}$-Cys-NH$_2$$^{46}$-GLP-1 (SEQ ID NO: 21).

In another embodiment, the GLP-1 compound is a GLP-1 fusion protein. In a preferred embodiment, the GLP-1 fusion protein comprises a GLP-1 portion and an Fc portion of an immunoglobulin. In a preferred embodiment, the GLP-1 fusion protein comprises a GLP-1 analog and the Fc portion of an immunoglobulin wherein the GLP-1 analog comprises an amino acid sequence of SEQ ID NO: 22

```
His Xaa Glu Gly Thr Phe Thr Ser Asp Val Ser Ser
        10                      15
Tyr Leu Glu Glu Gln Ala Ala Lys Glu Phe Ile Ala
    20                  25                  30
Trp Leu Xaa Xaa Gly Gly Xaa
            35
``` wherein
Xaa at position 8 is Gly or Val;
Xaa at position 33 is Val or Lys;
Xaa at position 34 is Lys or Asn;
Xaa at position 37 is Gly, Pro or is absent,
and wherein the GLP analog is fused to the Fc portion of an immunoglobulin comprising the amino acid sequence of Formula IV (SEQ ID NO: 23)

```
Ala Glu Ser Lys Tyr Gly Pro Pro Cys Pro Pro Cys
                5                   10
Pro Ala Pro Xaa Xaa Xaa Gly Gly Pro Ser Val Phe
            15                  20
Leu Phe Pro Pro Lys Pro Lys Asp Thr Leu Met Ile
25                  30                      35
Ser Arg Thr Pro Glu Val Thr Cys Val Val Val Asp
            40                  45
Val Ser Gln Glu Asp Pro Glu Val Gln Phe Asn Trp
    50                  53                      60
Tyr Val Asp Gly Val Glu Val His Asn Ala Lys Thr
            65                  70
Lys Pro Arg Glu Glu Gln Phe Xaa Ser Thr Tyr Arg
        75                  80
Val Val Ser Val Leu Thr Val Leu His Gln Asp Trp
85                  90                  95
Leu Asn Gly Lys Glu Tyr Lys Cys Lys Val Ser Asn
            100                 105
Lys Gly Leu Pro Ser Ser Ile Glu Lys Thr Ile Ser
    110                 115                 120
Lys Ala Lys Gly Gln Pro Arg Glu Pro Gln Val Tyr
            125                 130
Thr Leu Pro Pro Ser Gln Glu Glu Met Thr Lys Asn
        135                 140
Gln Val Ser Leu Thr Cys Leu Val Lys Gly Phe Tyr
145                 150                 155
Pro Ser Asp Ile Ala Val Glu Trp Glu Ser Asn Gly
            160                 165
Gln Pro Glu Asn Asn Tyr Lys Thr Thr Pro Pro Val
    170                 175                 180
Leu Asp Ser Asp Gly Ser Phe Phe Leu Tyr Ser Arg
            135                 190
Leu Thr Val Asp Lys Ser Arg Trp Gln Glu Gly Asn
        195                 200
Val Phe Ser Cys Ser Val Met His Glu Ala Leu His
205                 210                 215
Asn His Tyr Thr Gln Lys Ser Leu Ser Leu Ser Leu
            220                 225
Gly Xaa
    230
``` wherein:
Xaa at position 16 is Pro or Glu;
Xaa at position 17 is Phe, Val, or Ala;
Xaa at position 18 is Leu. Glu, or Ala;
Xaa at position 80 is Asn or Ala; and
Xaa at position 230 is Lys or is absent.

In a preferred embodiment, the C-terminus of the GLP-1 analog and the N-terminus of the Fc portion of an immunoglobulin are preferably fused together via 1, 1.5 (SEQ ID NO: 7) or 2 repeats (SEQ ID NO: 8) of a G-rich peptide linker having the sequence Gly-Gly-Gly-Gly-Ser-Gly-Gly-Gly-Gly-Ser-Gly-Gly-Gly-Gly-Ser (SEQ ID NO: 6).

In a preferred embodiment, the GLP-1 fusion protein comprises a GLP-1 analog and the Fc portion of an immunoglobulin wherein the GLP-1 analog consists of an amino acid sequence of SEQ ID NO: 22 and wherein the GLP analog is fused to the Fc portion of an immunoglobulin consisting of the amino acid sequence of SEQ ID NO: 23. In another embodiment, the GLP-1 fusion protein further comprises a linker. In another embodiment, the GLP-1 fusion protein further comprises a linker, wherein the linker comprises an amino acid sequence is selected from the group consisting of SEQ ID NO: 6, SEQ ID NO:7 and SEQ ID NO:8. In another embodiment, the GLP-1 fusion protein further comprises a linker, wherein the linker consists of an amino acid sequence is selected from the group consisting of SEQ ID NO: 6, SEQ ID NO:7 and SEQ ID NO:8. In an embodiment, the linker comprises an amino acid sequence of SEQ ID NO:6. In an embodiment, the linker comprises an amino acid sequence of SEQ ID NO:7. In an embodiment, the linker comprises an amino acid sequence of SEQ ID NO: 8. In an embodiment, the linker consists of an amino acid sequence of SEQ ID NO:6. In an embodiment, the linker consists of an amino acid sequence of SEQ ID NO:7. In an embodiment, the linker consists of an amino acid sequence of SEQ ID NO:8.

In an embodiment of the present invention, the GLP-1 portion comprises Gly $Xaa_8$. In another embodiment, the GLP-1 portion comprises Val at $Xaa_8$. In an embodiment, the GLP-1 portion comprises Gly at $Xaa_{22}$. In a preferred embodiment, the GLP-1 portion comprises Glu at $Xaa_{22}$. In an embodiment, the GLP-1 portion comprises Lys at $Xaa_{34}$. In another embodiment, the GLP-1 portion comprises Asn at $Xaa_{34}$. In an embodiment, $Xaa_{37}$ of the GLP-1 portion is absent. In a preferred embodiment, the GLP-1 portion comprises Gly at $Xaa_{37}$. In another preferred embodiment, the GLP-1 portion comprises Pro at $Xaa_{37}$.

Preferred GLP-1 fusion proteins of the present invention include the following proteins: $Gly^8$-$Glu^{22}$-$Gly^{36}$-GLP-1-1L-IgG4 (S228P) (SEQ ID NO: 24), $Gly^8$-$Glu^{22}$-$Gly^{36}$-GLP-1-1L-IgG4 (S228P, F234A, L235A) (SEQ ID NO: 25), $Glu^8$-$Glu^{22}$-$Gly^{36}$-GLP-1-1L-IgG4 (S228P, N297A) (SEQ ID NO: 26), $Gly^8$-$Glu^{22}$-$Gly^{36}$-GLP-1-1L-IgG4 (S228P, F234A, L235A, N297A) (SEQ ID NO: 27), $Gly^8$-$Glu^{22}$-$Gly^{36}$-GLP-1-1L-IgG4 (S228P, des K) (SEQ ID NO: 28). $Gly^8$-$Glu^{22}$-$Gly^{36}$-GLP-1-1L-IgG4 (S228P, F234A, L235A, des K) (SEQ ID NO: 29), $Gly^8$-$Glu^{22}$-$Gly^{36}$-GLP-1-1L-IgG4 (S228P, N297A, des K) (SEQ ID NO: 30), $Gly^8$-$Glu^{22}$-$Gly^{36}$-GLP-1-1L-IgG4 (S228P, F234A, L235A, N297A, des K) (SEQ ID NO: 31), $Gly^8$-$Glu^{22}$-$Gly^{36}$-GLP-1-1.5L-IgG4 (S228P) (SEQ ID NO: 32), $Gly^8$-$Glu^{22}$-$Gly^{36}$-GLP-1-1.5L-IgG4 (S228P, F234A, L235A) (SEQ ID NO: 33), $Gly^8$-$Glu^{22}$-$Gly^{36}$-GLP-1-1.5L-IgG4 (S228P, N297A) (SEQ ID NO: 34), $Gly^8$-$Glu^{22}$-$Gly^{36}$-GLP-1-1.5L-IgG4, (S228P, F234A, L235A, N297A) (SEQ ID NO: 35), $Gly^8$-$Glu^{22}$-$Gly^{36}$-GLP-1-1.5L-IgG4 (S228P, des K) (SEQ ID NO: 36), $Gly^8$-$Glu^{22}$-$Gly^{36}$-GLP-1-1.5L-IgG4 (S228P, F234A, L235A, des K) (SEQ ID NO: 37), $Gly^8$-$Glu^{22}$-$Gly^{36}$-GLP-1-1.5L-IgG4 (S228P, N297A des K) (SEQ ID NO: 38), $Gly^8$-$Glu^{22}$-$Gly^{36}$-GLP-1-1.5L-IgG4 (S228P, F234A, L235A, N297A, des K) (SEQ ID NO: 39), $Gly^8$-$Glu^{22}$-$Gly^{36}$-GLP-1-2L-IgG4 (S228P) (SEQ ID NO: 40), $Gly^8$-$Glu^{22}$-$Gly^{36}$-GLP-1-2L-IgG4 (S228P, F234A, L235A) (SEQ ID NO: 41), $Gly^8$-$Glu^{22}$-$Gly^{36}$-GLP-1-2L-IgG4 (S228P, N297A) (SEQ ID NO: 42), $Gly^8$-$Glu^{22}$-$Gly^{36}$-GLP-1-2L-IgG4 (S228P, F234A, L235A, N297A) (SEQ ID NO: 43), $Gly^8$-$Glu^{22}$-$Gly^{36}$-GLP-1-2L-IgG4 (S228P, des K) (SEQ ID NO: 44), $Gly^8$-$Glu^{22}$-$Gly^{36}$-GLP-1-2L-IgG4-(S228P, F234A, L235A, des K) (SEQ ID NO: 45), $Gly^8$-$Glu^{22}$-$Gly^{36}$-GLP-1-2L-IgG4 (S228P, N297A, des K) (SEQ ID NO: 46), $Gly^8$-$Glu^{22}$-$Gly^{36}$-GLP-1-2L-IgG4 (S228P, F234A, L235A, N297A, des K) (SEQ ID NO: 47), and the $Val^8$ forms of all of the above.

The present invention also includes FGF-21 compounds in combination with GLP-1 compounds, wherein the GLP-1 compound comprises an amino acid sequence selected from the group consisting of SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, and SEQ ID NO: 57. The present invention also includes FGF-21 compounds in combination with GLP-1 compounds, wherein the GLP-1 compound consists of an amino acid sequence selected from the group consisting of SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, and SEQ ID NO: 57.

Preferred FGF-21 compound and GLP-1 compound combinations of the present invention include, $Cys^{118}$-$Cys^{134}$-FGF-21 (SEQ ID NO: 9) in combination with $Val^8$-GLP-1 (SEQ ID NO: 15), $Cys^{118}$-$Cys^{134}$-FGF-21 (SEQ ID NO: 9) in combination with $Val^8$-$Glu^{22}$-GLP-1 (SEQ ID NO: 17), $Cys^{118}$-$Cys^{134}$-FGF-21, (SEQ ID NO: 9) in combination with is $Val^8$-$Glu^{22}$-$Ile^{33}$-$Gly^{36}$-$Pro^{37}$-$Ser^{38}$-$Ser^{39}$-$Gly^{40}$-$Ala^{41}$-$Pro^{42}$-$Pro^{43}$-$Pro^{44}$-$Ser^{45}$-GLP-1 (SEQ ID NO: 19), $Cys^{118}$-$Cys^{134}$-FGF-21 (SEQ ID NO: 9) in combination with pegylated $Val^8$-$Glu^{22}$-$Ile^{33}$-$Cys$-$NH_2^{46}$-GLP-1 (SEQ ID NO 21), $Cys^{118}$-$Cys^{134}$-FGF-21 (SEQ ID NO: 9) in combination with $Arg^{34}$-GLP-1 (SEQ ID NO: 16), $Cys^{118}$-$Cys^{134}$-FGF-21 (SEQ ID NO: 9) in combination with acylated $Arg^{34}$-GLP-1 (SEQ ID NO: 16), $Cys^{118}$-$Cys^{134}$-FGF-21 (SEQ ID NO: 9) in combination with $Arg^{34}$-$Lys^{26}$-(N-ε-(γ-Glu (N-α-hexadecanoyl)))-GLP-1 (SEQ ID NO: 18), $Cys^{118}$-$Cys^{134}$-FGF-21 (SEQ ID NO: 9) in combination with $Gly^8$-$Glu^{22}$-$Gly^{36}$-GLP-1-1L-IgG4 (S228P) (SEQ ID NO: 24), $Cys^{118}$-$Cys^{134}$-FGF-21 (SEQ ID NO: 9) in combination with $Gly^8$-$Glu^{22}$-$Gly^{36}$-GLP-1-1L-IgG4 (S228P, F234A, L235A) (SEQ ID NO: 25), $Cys^{118}$-$Cys^{134}$-FGF-21 (SEQ ID NO: 9) in combination with $Gly^8$-$Glu^{22}$-$Gly^{36}$-GLP-1-1L-IgG4 (S228P, N297A) (SEQ ID NO: 26), $Cys^{118}$-$Cys^{134}$-FGF-21 (SEQ ID NO: 9) in combination with $Gly^8$-$Glu^{22}$-$Gly^{36}$-GLP-1-1L-IgG4 (S228P, F234A, L235A, N297A) (SEQ ID NO: 27), $Cys^{118}$-$Cys^{134}$-FGF-21 (SEQ ID NO: 9) in combination with $Gly^8$-$Glu^{22}$-$Gly^{36}$-GLP-1-1L-IgG4 (S228P, des K) (SEQ ID NO: 28), $Cys^{118}$-$Cys^{134}$-FGF-21 (SEQ ID NO: 9) in combination with $Gly^8$-$Glu^{22}$-$Gly^{36}$-GLP-1-1L-IgG4 (S228P, F234A, L235A, des K) (SEQ ID NO: 29), $Cys^{118}$-$Cys^{134}$-FGF-21 (SEQ ID NO: 9) in combination with $Gly^8$-$Glu^{22}$-$Gly^{36}$-GLP-1-1L-IgG4 (S228P, N297A, des K) (SEQ ID NO: 30), $Cys^{118}$-$Cys^{134}$-FGF-21 (SEQ ID NO: 9) in combination with $Gly^8$-$Glu^{22}$-$Gly^{36}$-GLP-1-1L-IgG4 (S228P, F234A, L235A, N297A, des K) (SEQ ID NO: 31), $Cys^{118}$-$Cys^{134}$-FGF-21 (SEQ ID NO: 9) in combination with $Gly^8$-$Glu^{22}$-$Gly^{36}$-GLP-1-1.5L-IgG4 (S228P) (SEQ ID NO: 32), $Cys^{118}$-$Cys^{134}$-FGF-21 (SEQ ID NO: 9) in combination with $Gly^8$-$Glu^{22}$-$Gly^{36}$-GLP-1-1.5L-IgG4 (S228P, F234A, L235A) (SEQ ID NO: 33), $Cys^{118}$-$Cys^{134}$-FGF-21 (SEQ ID NO: 9) in combination with $Gly^8$-$Glu^{22}$-$Gly^{36}$-GLP-1-1.5L-IgG4 (S228P, N297A) (SEQ ID NO: 34), $Cys^{118}$-$Cys^{134}$-FGF-21 (SEQ ID NO: 9) in combination with $Gly^8$-$Glu^{22}$-$Gly^{36}$-GLP-1-1.5L-IgG4 (S228P, F234A, L235A, N297A) (SEQ ID NO: 35), $Cys^{118}$-$Cys^{134}$-FGF-21 (SEQ ID NO: 9) in combination with $Gly^8$-$Glu^{22}$-$Gly^{36}$-GLP-1-1.5L-IgG4 (S228P, des K) (SEQ ID NO: 36), $Cys^{118}$-$Cys^{134}$-FGF-21 (SEQ ID NO: 9) in combination with $Gly^8$-$Glu^{22}$-$Gly^{36}$-GLP-1-1.5L-IgG4 (S228P, F234A, L235A, des K) (SEQ ID NO: 37), $Cys^{118}$-$Cys^{134}$-FGF-21 (SEQ ID NO: 9) in combination with $Gly^{118}$-$Glu^{22}$-$Gly^{36}$-GLP-1-1.5L-IgG4 (S228P, N297A, des K) (SEQ ID NO: 38), Cys$^{118}$-Cys$^{134}$-FGF-21 (SEQ ID NO: 9) in combination with Gly$^8$-Glu$^{22}$-Gly$^{36}$-GLP-1-1.5L-IgG4 (S228P, F234A, L235A, N297A, des K) (SEQ ID NO: 39), Cys$^{118}$-Cys$^{134}$-FGF-21 (SEQ ID NO: 9) in combination with Gly$^8$-Glu$^{22}$-Gly$^{36}$-GLP-1-2L-IgG4 (S228P) (SEQ ID NO: 40), Cys$^{118}$-Cys$^{134}$-FGF-21 (SEQ ID NO: 9) in combination with Gly$^8$-Glu$^{22}$-Gly$^{36}$-GLP-1-2L-IgG4 (S228P, F234A, L235A) (SEQ ID NO: 41), Cys$^{118}$-Cys$^{134}$-FGF-21 (SEQ ID NO: 9) in combination with Gly$^8$-Glu$^{22}$-Gly$^{36}$-GLP-1-2L-IgG4 (S228P, N297A) (SEQ ID NO: 42), Cys$^{118}$-Cys$^{134}$-FGF-21 (SEQ ID NO: 9) in combination with Gly$^8$-Glu$^{22}$-Glu$^{36}$-GLP-1-2L-IgG4 (S228P, F234A, L235A, N297A) (SEQ ID NO: 43), Cys$^{118}$-Cys$^{134}$-FGF-21 (SEQ ID NO: 9) in combination with Gly$^8$-Glu$^{22}$-Gly$^{36}$-GLP-1-2L-IgG4 (S228P, des K) (SEQ ID NO: 44), Cys$^{118}$-Cys$^{134}$-FGF-21 (SEQ ID NO: 9) in combination with Gly$^8$-Glu$^{22}$-Gly$^{36}$-GLP-1-2L-IgG4 (S228P, F234A, L235A, des K) (SEQ ID NO: 45), Cys$^{118}$-Cys$^{134}$-FGF-21 (SEQ ID NO: 9) in combination with Gly$^8$-Glu$^{22}$-Gly$^{36}$-GLP-1-2L-IgG4 (S228P, N297A, des K) (SEQ ID NO: 46), Cys$^{118}$-Cys$^{134}$-FGF-21 (SEQ ID NO: 9) in combination with Gly$^8$-Glu$^{22}$-Gly$^{36}$-GLP-1-2L-IgG4 (S228P, F234A, L235A, N297A, des K) (SEQ ID NO: 47), Cys$^{118}$-Cys$^{134}$-FGF-21 (SEQ ID NO: 9) in combination with exendin-4 (SEQ ID NO: 4), Cys$^{118}$-Cys$^{134}$-FGF-21 (SEQ ID NO: 9) in combination with albiglutide (SEQ ID NO: 48). Cys$^{118}$-Cys$^{134}$-FGF-21 (SEQ ID NO: 9) in combination with a GLP-1 compound comprising the amino acid sequence of SEQ ID NO: 47, Cys$^{118}$-Cys$^{134}$-FGF-21 (SEQ ID NO: 9) in combination with a GLP-1 compound consisting of the amino acid sequence of SEQ ID NO: 47, Cys$^{118}$-Cys$^{134}$-FGF-21 (SEQ ID NO: 9) in combination with a GLP-1 compound comprising the amino acid sequence of SEQ ID NO: 48, Cys$^{118}$-Cys$^{134}$-FGF-21 (SEQ ID NO: 9) in combination with a GLP-1 compound consisting of the amino acid sequence of SEQ ID NO: 48, Cys$^{118}$-Cys$^{134}$-FGF-21 (SEQ ID NO: 9) in combination with a GLP-1 compound comprising the amino acid sequence of SEQ ID NO: 49, Cys$^{118}$-Cys$^{134}$-FGF-21 (SEQ ID NO: 9) in combination with a GLP-1 compound consisting of the amino acid sequence of SEQ ID NO: 49, Cys$^{118}$-Cys$^{134}$-FGF-21 (SEQ ID NO: 9) in combination with a GLP-1 compound comprising the amino acid sequence of SEQ ID NO: 50, Cys$^{118}$-Cys$^{134}$-FGF-21 (SEQ ID NO: 9) in combination with a GLP-1 compound consisting of the amino acid sequence of SEQ ID NO: 50, Cys$^{118}$-Cys$^{134}$-FGF-21 (SEQ ID NO: 9) in combination with a GLP-1 compound comprising the amino acid sequence of SEQ ID NO: 51, Cys$^{118}$-Cys$^{134}$-FGF-21 (SEQ ID NO: 9) in combination with a GLP-1 compound consisting of the amino acid sequence of SEQ ID NO: 51, Cys$^{118}$-Cys$^{134}$-FGF-21 (SEQ ID NO: 9) in combination with a GLP-1 compound comprising the amino acid sequence of SEQ ID NO: 52, Cys$^{118}$-Cys$^{134}$-FGF-21 (SEQ ID NO: 9) in combination with a GLP-1 compound consisting of the amino acid sequence of SEQ ID NO: 52, Cys$^{118}$-Cys$^{134}$-FGF-21 (SEQ ID NO: 9) in combination with a GLP-1 compound comprising the amino acid sequence of SEQ ID NO: 53, Cys$^{118}$-Cys$^{134}$-FGF-21 (SEQ ID NO: 9) in combination with a GLP-1 compound consisting of the amino acid sequence of SEQ ID NO: 53, Cys$^{118}$-Cys$^{134}$-FGF-21 (SEQ ID NO: 9) in combination with a GLP-1 compound comprising the amino acid sequence of SEQ ID NO: 54, Cys$^{118}$-Cys$^{134}$-FGF-21 (SEQ ID NO: 9) in combination with a GLP-1 compound consisting of the amino acid sequence of SEQ ID NO: 54, Cys$^{118}$-Cys$^{134}$-FGF-21 (SEQ ID NO: 9) in combination with a GLP-1 compound comprising the amino acid sequence of SEQ ID NO: 55, Cys$^{118}$-Cys$^{134}$-FGF-21 (SEQ ID NO: 9) in combination with a GLP-1 compound consisting of the amino acid sequence of SEQ ID NO: 55, Cys$^{118}$-Cys$^{134}$-FGF-21 (SEQ ID NO: 9) in combination with a GLP-1 compound comprising the amino acid sequence of SEQ ID NO: 56, Cys$^{118}$-Cys$^{134}$-FGF-21 (SEQ ID NO: 9) in combination with a GLP-1 compound consisting of the amino acid sequence of SEQ ID NO: 56, Cys$^{118}$-Cys$^{134}$-FGF-21 (SEQ ID NO: 9) in combination with a GLP-1 compound comprising the amino acid sequence of SEQ ID NO: 57, and Cys$^{118}$-Cys$^{134}$-FGF-21 (SEQ ID NO: 9) in combination with a GLP-1 compound consisting of the amino acid sequence of SEQ ID NO: 57

In a preferred embodiment, the combination of the present invention comprises an FGF-21 analog comprising the amino acid sequence of Cys$^{118}$-Cys$^{134}$-FGF-21 (SEQ ID NO: 9) in combination with a GLP-1 analog, wherein the GLP-1 analog comprises the amino acid sequence of Val$^8$-Glu$^{22}$-GLP-1 (SEQ ID NO: 17) with five additional amino acid sequence substitutions. In a preferred embodiment, the combination of the present invention comprises an FGF-21 analog consisting of the amino acid sequence of Cys$^{118}$-Cys$^{134}$-FGF-21 (SEQ ID NO: 9) in combination with a GLP-1 analog, wherein the GLP-1 analog consists of the amino acid sequence of Val$^8$-Glu$^{22}$-GLP-1 (SEQ ID NO: 17) with five additional amino acid sequence substitutions. In another preferred embodiment, the combination of the present invention comprises an FGF-21 analog comprising the amino acid sequence of Cys$^{118}$-Cys$^{134}$-FGF-21 (SEQ ID NO: 9) in combination with a GLP-1 analog, wherein the GLP-1 analog comprises the amino acid sequence of Val$^8$-Glu$^{22}$-GLP-1 (SEQ ID NO: 17) with four additional amino acid sequence substitutions. In another preferred embodiment, the combination of the present invention comprises an FGF-21 analog consisting of the amino acid sequence of Cys$^{118}$-Cys$^{134}$-FGF-21 (SEQ ID NO: 9) in combination with a GLP-1 analog, wherein the GLP-1 analog consists of the amino acid sequence of Val$^8$-Glu$^{22}$-GLP-1 (SEQ ID NO: 17) with four additional amino acid sequence substitutions. In another preferred embodiment, the combination of the present invention comprises an FGF-21 analog comprising the amino acid sequence of Cys$^{118}$-Cys$^{134}$-FGF-21 (SEQ ID NO: 9) in combination with a GLP-1 analog, wherein the GLP-1 analog comprises the amino acid sequence of Val$^8$-Glu$^{22}$-GLP-1 (SEQ ID NO: 17) with three additional amino acid sequence substitutions. In another preferred embodiment, the combination of the present invention comprises an FGF-21 analog consisting of the amino acid sequence of Cys$^{118}$-Cys$^{134}$-FGF-21 (SEQ ID NO: 9) in combination with a GLP-1 analog, wherein the GLP-1 analog consists of the amino acid sequence of Val$^8$-Glu$^{22}$-GLP-1 (SEQ ID NO: 17) with three additional amino acid sequence substitutions. In another preferred embodiment, the combination of the present invention comprises an FGF-21 analog comprising the amino acid sequence of Cys$^{118}$-Cys$^{134}$-FGF-21 (SEQ ID NO: 9) in combination with a GLP-1 analog, wherein the GLP-1 analog comprises the amino acid sequence of Val$^8$-Glu$^{22}$-GLP-1 (SEQ ID NO: 17) with two additional amino acid sequence substitutions. In another preferred embodiment, the combination of the present invention comprises an FGF-21 analog consisting of the amino acid sequence of Cys$^{118}$-Cys$^{134}$-FGF-21 (SEQ ID NO: 9) in combination with a GLP-1 analog, wherein the GLP-1 analog consists of the amino acid sequence of Val$^8$-Glu$^{22}$-GLP-1 (SEQ ID NO: 17) with two additional amino acid sequence substitutions. In another preferred embodiment, the combination of the present invention comprises an FGF-21 analog comprising the amino acid sequence of Cys$^{118}$-Cys$^{134}$-FGF-21 (SEQ ID NO: 9) in combination with a GLP-1 analog, wherein the GLP-1 analog comprises the amino acid sequence of Val$^8$-Glu$^{22}$-GLP-1 (SEQ ID NO: 17)

with one additional amino acid sequence substitution. In another preferred embodiment, the combination of the present invention comprises an FGF-21 analog consisting of the amino acid sequence of $Cys^{118}$-$Cys^{134}$-FGF-21 (SEQ ID NO: 9) in combination with a GLP-1 analog, wherein the GLP-1 analog consists of the amino acid sequence of $Val^8$-$Glu^{22}$-GLP-1 (SEQ ID NO: 17) with one additional amino acid sequence substitution.

More preferred FGF-21 compound and GLP-1 compound combinations of the present invention include $Cys^{118}$-$Cys^{134}$-FGF-21 (SEQ ID NO: 10) in combination with $Val^8$-GLP-1 (SEQ ID NO: 17), $Cys^{118}$-$Cys^{134}$-$Ala^{167}$-FGF-21 (SEQ ID NO: 10) in combination with $Val^8$-$Glu^{22}$-GLP-1 (SEQ ID NO: 17), $Cys^{118}$-$Cys^{134}$-FGF-21 (SEQ ID NO: 10) in combination with is $Val^8$-$Glu^{22}$-$Ile^{33}$-$Gly^{36}$-$Pro^{37}$-$Ser^{38}$-$Ser^{39}$-$Gly^{40}$-$Ala^{41}$-$Pro^{42}$-$Pro^{43}$-$Pro^{44}$-$Ser^{45}$-GLP-1 (SEQ ID NO: 19), $Cys^{118}$-$Cys^{134}$-$Ala^{167}$-FGF-21 (SEQ ID NO: 10) in combination with pegylated $Val^8$-$Glu^{22}$-$Ile^{33}$-$Cys$-$NH_2^{46}$-GLP-1 (SEQ ID NO: 21), $Cys^{118}$-$Cys^{134}$-$Ala^{167}$-FGF-21 (SEQ ID NO: 10) in combination with $Arg^{34}$-GLP-1 (SEQ ID NO: 16), $Cys^{118}$-$Cys^{134}$-$Ala^{167}$-FGF-21 (SEQ ID NO: 10) in combination with acylated $Arg^{34}$-GLP-1 (SEQ ID NO: 16), $Cys^{118}$-$Cys^{134}$-$Ala^{167}$-FGF-21 (SEQ ID NO: 10) in combination, with $Arg^{34}$-$Lys^{26}$-(N-ε-(γ-Glu(N-α-hexadecanoyl)))-GLP-1 (SEQ ID NO: 18), $Cys^{118}$-$Cys^{134}$-$Ala^{167}$-FGF-21 (SEQ ID NO: 10) in combination with $Gly^8$-$Glu^{22}$-$Gly^{36}$-GLP-1(7-37)-1L-IgG4 (S228P) (SEQ ID NO: 24), $Cys^{118}$-$Cys^{134}$-$Ala^{167}$-FGF-21 (SEQ ID NO: 10) in combination with $Gly^8$-$Glu^{22}$-$Gly^{36}$-GLP-1(7-37)-1L-IgG4 (S228P, F234A, L235A) (SEQ ID NO: 25), $Cys^{118}$-$Cys^{134}$-$Ala^{167}$-FGF-21 (SEQ ID NO:10) in combination with $Gly^8$-$Glu^{22}$-$Gly^{36}$-GLP-1(7-37)-1L-IgG4 (S228P, N297A) (SEQ ID NO: 26), $Cys^{118}$-$Cys^{134}$-$Ala^{167}$-FGF-21 (SEQ ID NO: 10) in combination with $Gly^8$-$Glu^{22}$-$Gly^{36}$-GLP-1(7-37)-1L-IgG4 (S228P, F234A, L235A, N297A) (SEQ ID NO: 27), $Cys^{118}$-$Cys^{134}$-$Ala^{167}$-FGF-21 (SEQ ID NO: 10) in combination with $Gly^8$-$Glu^{22}$-$Gly^{36}$-GLP-1(7-37)-1L-IgG4 (S228P, des K) (SEQ ID NO: 28), $Cys^{118}$-$Cys^{134}$-$Ala^{167}$-FGF-21 (SEQ ID NO: 10) in combination with $Gly^8$-$Glu^{22}$-$Gly^{36}$-GLP-1(7-37)-1L-IgG4 (S228P, F234A, L235A, des K) (SEQ ID NO: 29), $Cys^{118}$-$Cys^{134}$-$Ala^{167}$-FGF-21 (SEQ ID NO:10) in combination with $Gly^8$-$Glu^{22}$-$Gly^{36}$-GLP-1(7-37)-1L-IgG4 (S228P, N297A, des K) (SEQ ID NO: 30), $Cys^{118}$-$Cys^{134}$-$Ala^{167}$-FGF-21 (SEQ ID NO:10) in combination with $Gly^8$-$Glu^{22}$-$Gly^{36}$-GLP-1(7-37)-1L-IgG4 (S228P, F234A, L235A, N297A, des K) (SEQ ID NO: 31), $Cys^{118}$-$Cys^{134}$-$Ala^{167}$-FGF-21 (SEQ ID NO: 10) in combination with $Gly^8$-$Glu^{22}$-$Gly^{36}$-GLP-1(7-37)-1.5L-IgG4 (S228P) (SEQ ID NO: 32), $Cys^{118}$-$Cys^{134}$-$Ala^{167}$-FGF-21 (SEQ ID NO:10) in combination with $Gly^8$-$Glu^{22}$-$Gly^{36}$-GLP-1(7-37)-1.5L-IgG4 (S228P, F234A, L235A) (SEQ ID NO: 33), $Cys^{118}$-$Cys^{134}$-$Ala^{167}$-FGF-21 (SEQ ID NO:10) in combination with $Gly^8$-$Glu^{22}$-$Gly^{36}$-GLP-1(7-37)-1.5L-IgG4 (S228P, N297A) (SEQ ID NO: 34), $Cys^{118}$-$Cys^{134}$-$Ala^{167}$-FGF-21 (SEQ ID NO:10) in combination with $Gly^8$-$Glu^{22}$-$Gly^{36}$-GLP-1-1.5L-IgG4 (S228P, F234A, L235A, N297A) (SEQ ID NO: 35), $Cys^{118}$-$Cys^{134}$-$Ala^{167}$-FGF-21 (SEQ ID NO:10) in combination with $Gly^8$-$Glu^{22}$-$Gly^{36}$-GLP-1(7-37)-1.5L-IgG4 (S228P, des K) (SEQ ID NO: 36), $Cys^{118}$-$Cys^{134}$-$Ala^{167}$-FGF-21 (SEQ ID NO: 10) in combination with $Gly^8$-$Glu^{22}$-$Gly^{36}$-GLP-1(7-37)-1.5L-IgG4 (S228P, F234A, L235A, des K) (SEQ ID NO: 37), $Cys^{118}$-$Cys^{134}$-$Ala^{167}$-FGF-21 (SEQ ID NO:10) in combination with $Gly^8$-$Glu^{22}$-$Gly^{36}$-GLP-1(7-37)-1.5L-IgG4 (S228P, N297A, des K) (SEQ ID NO: 38), $Cys^{118}$-$Cys^{134}$-$Ala^{167}$-FGF-21 (SEQ ID NO:10) in combination with $Gly^8$-$Glu^{22}$-$Gly^{36}$-GLP-1-1.5L-IgG4 (S228P, F234A, L235A, N297A, des K) (SEQ ID NO: 39), $Cys^{118}$-$Cys^{134}$-$Ala^{167}$-FGF-21 (SEQ ID NO:10) in combination with $Gly^8$-$Glu^{22}$-$Gly^{36}$-GLP-1-2L-IgG4 (S228P) (SEQ ID NO: 40), $Cys^{118}$-$Cys^{134}$-$Ala^{167}$-FGF-21 (SEQ ID NO:10) in combination with $Gly^8$-$Glu^{22}$-$Gly^{36}$-GLP-1-2L-IgG4 (S228P, F234A, L235A) (SEQ ID NO: 41), $Cys^{118}$-$Cys^{134}$-$Ala^{167}$-FGF-21 (SEQ ID NO: 10) in combination with $Gly^8$-$Glu^{22}$-$Gly^{36}$-GLP-1-2L-IgG4 (S228P, N297A) (SEQ ID NO: 42), $Cys^{118}$-$Cys^{134}$-$Ala^{167}$-FGF-21 (SEQ ID NO:10) in combination with $Gly^8$-$Glu^{22}$-$Gly^{36}$-GLP-1(7-37)-2L-IgG4 (S228P, F234A, L235A, N297A) (SEQ ID NO: 43), $Cys^{118}$-$Cys^{134}$-$Ala^{167}$-FGF-21 (SEQ ID NO:10) in combination with $Gly^8$-$Glu^{22}$-$Gly^{36}$-GLP-1-2L-IgG4 (S228P, des K) (SEQ ID NO: 44), $Cys^{118}$-$Cys^{134}$-$Ala^{167}$-FGF-21 (SEQ ID NO:10) in combination with $Gly^8$-$Glu^{22}$-$Gly^{36}$-GLP-1-2L-IgG4 (S228P, F234A, L235A, des K) (SEQ ID NO: 45), $Cys^{118}$-$Cys^{134}$-$Ala^{167}$-FGF-21 (SEQ ID NO: 10) in combination with $Gly^8$-$Glu^{22}$-$Gly^{36}$-GLP-1-2L-IgG4 (S228P, N297A, des K) (SEQ ID NO: 46), $Cys^{118}$-$Cys^{134}$-$Ala^{167}$-FGF-21 (SEQ ID NO:10) in combination with $Gly^8$-$Glu^{22}$-$Gly^{36}$-GLP-1(7-37)-2L-IgG4 (S228P, F234A, L235A, N297A, des K) (SEQ ID NO: 47), $Cys^{118}$-$Cys^{134}$-$Ala^{167}$-FGF-21 (SEQ ID NO:10) in combination with exendin-4 (SEQ ID NO: 4), $Cys^{118}$-$Cys^{134}$-$Ala^{167}$-FGF-21 (SEQ ID NO:10) in combination with albiglutide (SEQ ID NO: 48), $Cys^{118}$-$Cys^{134}$-$Ala^{167}$-FGF-21 (SEQ ID NO:10) in combination with a GLP-1 compound comprising the amino acid sequence of SEQ ID NO: 47, $Cys^{118}$-$Cys^{134}$-$Ala^{167}$-FGF-21 (SEQ ID NO:10) in combination with a GLP-1 compound consisting of the amino acid sequence of SEQ ID NO: 47, $Cys^{118}$-$Cys^{134}$-$Ala^{167}$-FGF-21 (SEQ ID NO: 10) in combination with a GLP-1 compound comprising the amino acid sequence of SEQ ID NO: 48, $Cys^{118}$-$Cys^{134}$-$Ala^{167}$-FGF-21 (SEQ ID NO:10) in combination with a GLP-1 compound consisting of the amino acid sequence of SEQ ID NO: 48, $Cys^{118}$-$Cys^{134}$-$Ala^{167}$-FGF-21 (SEQ ID NO:10) in combination with a GLP-1 compound comprising the amino acid sequence of SEQ ID NO: 49, $Cys^{118}$-$Cys^{134}$-$Ala^{167}$-FGF-21 (SEQ ID NO:10) in combination with a GLP-1 compound consisting of the amino acid sequence of SEQ ID NO: 49, $Cys^{118}$-$Cys^{134}$-$Ala^{167}$-FGF-21 (SEQ ID NO:10) in combination with a GLP-1 compound comprising the amino acid sequence of SEQ ID NO: 50, $Cys^{118}$-$Cys^{134}$-$Ala^{167}$-FGF-21 (SEQ ID NO:10) in combination with a GLP-1 compound consisting of the amino acid sequence of SEQ ID NO: 50, $Cys^{118}$-$Cys^{134}$-$Ala^{167}$-FGF-21 (SEQ ID NO: 10) in combination with a GLP-1 compound comprising the amino acid sequence of SEQ ID NO: 51, $Cys^{118}$-$Cys^{134}$-$Ala^{167}$-FGF-21 (SEQ ID NO:10) in combination with a GLP-1 compound consisting of the amino acid sequence of SEQ ID NO: 51, $Cys^{118}$-$Cys^{134}$-$Ala^{167}$-FGF-21 (SEQ ID NO:10) in combination with a GLP-1 compound comprising, the amino acid sequence of SEQ ID NO: 52, $Cys^{118}$-$Cys^{134}$-$Ala^{167}$-FGF-21 (SEQ ID NO:10) in combination with a GLP-1 compound consisting of the amino acid sequence of SEQ ID NO: 52, $Cys^{118}$-$Cys^{134}$-$Ala^{167}$-FGF-21 (SEQ ID NO:10) in combination with a GLP-1 compound comprising the amino acid sequence of SEQ ID NO: 53, $Cys^{118}$-$Cys^{134}$-$Ala^{167}$-FGF-21 (SEQ ID NO:10) in combination with a GLP-1 compound consisting of the amino acid sequence of SEQ ID NO: 53, $Cys^{118}$-$Cys^{134}$-$Ala^{167}$-FGF-21 (SEQ ID NO:10) in combination with a GLP-1 compound comprising the amino acid sequence of SEQ ID NO: 54, $Cys^{118}$-$Cys^{134}$-$Ala^{167}$-FGF-21 (SEQ ID NO: 10) in combination with a GLP-1 compound consisting of the amino acid sequence of SEQ ID NO: 54, $Cys^{118}$-$Cys^{134}$-$Ala^{167}$-FGF-21 (SEQ ID NO:10) in combination with a GLP-1 compound comprising the amino acid sequence of SEQ ID NO: 55, $Cys^{118}$-$Cys^{134}$-$Ala^{167}$-FGF-21 (SEQ ID NO: 10) in combination with a GLP-1 compound consisting of the amino acid sequence of SEQ ID NO: 55, $Cys^{118}$-$Cys^{134}$-$Ala^{167}$-FGF-21 (SEQ ID NO:10) in combination with a GLP-1 compound comprising the amino acid sequence of SEQ ID NO: 56, $Cys^{118}$-$Cys^{134}$-$Ala^{167}$-FGF-21 (SEQ ID NO:10) in combination with a GLP-1 compound consisting of the amino acid sequence of SEQ ID NO: 56, $Cys^{118}$-$Cys^{134}$-$Ala^{167}$-FGF-21 (SEQ ID NO:10) in combination with a GLP-1 compound comprising the amino acid sequence of SEQ ID NO: 57 and $Cys^{118}$-$Cys^{134}$-$Ala^{167}$-FGF-21 (SEQ ID NO:10) in combination with a GLP-1 compound consisting of the amino acid sequence of SEQ ID NO: 57.

In a preferred embodiment, the combination of the present invention comprises an FGF-21 analog comprising the amino acid sequence of $Cys^{118}$-$Cys^{134}$-$Ala^{167}$-FGF-21 (SEQ ID NO: 10) in combination with a GLP-1 analog, wherein the GLP-1 analog comprises the amino acid sequence of $Val^8$-$Glu^{22}$-GLP-1 (SEQ ID NO: 17) with five additional amino acid sequence substitutions. In a preferred embodiment, the combination of the present invention comprises an FGF-21 analog consisting of the amino acid sequence of $Cys^{118}$-$Cys^{134}$-$Ala^{167}$-FGF-21 (SEQ ID NO: 10) in combination with a GLP-1 analog, wherein the GLP-1 analog consists of the amino acid sequence of $Val^8$-$Glu^{22}$-GLP-1 (SEQ ID NO: 17) with five additional amino acid sequence substitutions. In another preferred embodiment, the combination of the present invention comprises an FGF-21 analog comprising the amino acid sequence of $Cys^{118}$-$Cys^{134}$-$Ala^{167}$-FGF-21 (SEQ ID NO: 10) in combination with a GLP-1 analog, wherein the GLP-1 analog comprises the amino acid sequence of $Val^8$-$Glu^{22}$-GLP-1 (SEQ ID NO: 17) with four additional amino acid sequence substitutions. In another preferred embodiment, the combination of the present invention comprises an FGF-21 analog consisting of the amino acid sequence of $Cys^{118}$-$Cys^{134}$-$Ala^{167}$-FGF-21 (SEQ ID NO: 10) in combination with a GLP-1 analog, wherein the GLP-1 analog consists of the amino acid sequence of $Val^8$-$Glu^{22}$-GLP-1 (SEQ ID NO: 17) with four additional amino acid sequence substitutions. In another preferred embodiment, the combination of the present invention comprises an FGF-21 analog comprising the amino acid sequence of $Cys^{118}$-$Cys^{134}$-$Ala^{167}$-FGF-21 (SEQ ID NO: 10) in combination with a GLP-1 analog, wherein the GLP-1 analog comprises an amino acid sequence of $Val^8$-$Glu^{22}$-GLP-1 (SEQ ID NO: 17) with three additional amino acid sequence substitutions. In another preferred embodiment, the combination of the present invention comprises an FGF-21 analog consisting of the amino acid sequence of $Cys^{118}$-$Cys^{134}$-$Ala^{167}$-FGF-21 (SEQ ID NO: 10) in combination with a GLP-1 analog, wherein the GLP-1 analog consist of an amino acid sequence of $Val^8$-$Glu^{22}$-GLP-1 (SEQ ID NO: 17) with three additional amino acid sequence substitutions. In another preferred embodiment, the combination of the present invention comprises an FGF-21 analog comprising the amino acid sequence of $Cys^{118}$-$Cys^{134}$-$Ala^{167}$-FGF-21 (SEQ ID NO: 10) in combination with a GLP-1 analog, wherein the GLP-1 analog comprises the amino acid sequence of $Val^8$-$Glu^{22}$-GLP-1 (SEQ ID NO: 17) with two additional amino acid sequence substitutions. In another preferred combination of the present invention comprises an FGF-21 analog consisting of the amino acid sequence of $Cys^{118}$-$Cys^{134}$-$Ala^{167}$-FGF-21 (SEQ ID NO: 10) in combination with a GLP-1 analog, wherein the GLP-1 analog consists of the amino acid sequence of $Val^8$-$Glu^{22}$-GLP-1 (SEQ ID NO: 17) with two additional amino acid sequence substitutions. In another preferred embodiment, the combination of the present invention comprises an FGF-21 analog comprising the amino acid sequence of $Cys^{118}$-$Cys^{134}$-$Ala^{167}$-FGF-21 (SEQ ID NO: 10) in combination with a GLP-1 analog, wherein the GLP-1 analog comprises the amino acid sequence of $Val^8$-$Glu^{22}$-GLP-1 (SEQ ID NO: 17) with one additional amino acid sequence substitution. In another preferred embodiment, the combination of the present invention comprises an FGF-21 analog consisting of the amino acid sequence of $Cys^{118}$-$Cys^{134}$-$Ala^{167}$-FGF-21 (SEQ ID NO: 10) in combination with a GLP-1 analog, wherein the GLP-1 analog consists of the amino acid sequence of $Val^8$-$Glu^{22}$-GLP-1 (SEQ ID NO: 17) with one additional amino acid sequence substitution.

Preferred FGF-21 compound and GLP-1 compound combinations of the present invention include, $Cys^{118}$-$Cys^{134}$-$Ala^{167}$-FGF-21 (SEQ ID NO: 13) in combination with $Val^8$-GLP-1 (SEQ ID NO: 15), $Cys^{118}$-$Cys^{134}$-$Ala^{167}$-FGF-21 (SEQ ID NO: 13) in combination with $Val^8$-$Glu^{22}$-GLP-1 (SEQ ID NO: 17), $Cys^{118}$-$Cys^{134}$-$Ala^{121}$-$Ala^{167}$-FGF-21 (SEQ ID NO: 13) in combination with is $Val^8$-$Glu^{22}$-$Ile^{33}$-$Gly^{36}$-$Pro^{37}$-$Ser^{38}$-$Ser^{39}$-$Gly^{40}$-$Ala^{41}$-$Pro^{42}$-$Pro^{43}$-$Pro^{44}$-$Ser^{45}$-GLP-1 (SEQ ID NO: 19), $Cys^{118}$-$Cys^{134}$-$Ala^{121}$-$Ala^{167}$-FGF-21 (SEQ ID NO: 13) in combination with pegylated $Val^8$-$Glu^{22}$-$Ile^{33}$-$Cys$-$NH_2^{46}$-GLP-1 (SEQ ID NO: 21), $Cys^{118}$-$Cys^{134}$-$Ala^{121}$-$Ala^{167}$-FGF-21 (SEQ ID NO: 13) in combination with $Arg^{34}$-GLP-1 (SEQ ID NO: 16), $Cys^{118}$-$Cys^{134}$-$Ala^{121}$-$Ala^{167}$-FGF-21 (SEQ ID NO: 13) in combination with acylated $Arg^{34}$-GLP-1 (SEQ ID NO: 16), $Cys^{118}$-$Cys^{134}$-$Ala^{121}$-$Ala^{167}$-FGF-21 (SEQ ID NO: 13) in combination with $Arg^{34}$-$Lys^{26}$-(N-ε-(γ-Glu(N-α-hexadecanoyl)))-GLP-1 (SEQ ID NO: 18), $Cys^{118}$-$Cys^{134}$-$Ala^{121}$-$Ala^{167}$-FGF-21 (SEQ ID NO: 13) in combination with $Gly^8$-$Glu^{22}$-$Gly^{36}$-GLP-1-1L-IgG4 (S228P) (SEQ ID NO: 24), $Cys^{118}$-$Cys^{134}$-$Ala^{121}$-$Ala^{167}$-FGF-21 (SEQ ID NO: 13) with $Gly^8$-$Glu^{22}$-$Gly^{36}$-GLP-1-1L-IgG4 (S228P, F234A, L235A) (SEQ ID NO: 25), $Cys^{118}$-$Cys^{134}$-$Ala^{121}$-$Ala^{167}$-FGF-21 (SEQ ID NO: 13) in combination with $Gly^8$-$Glu^{22}$-$Gly^{36}$-GLP-1-1L-IgG4 (S228P, N297A) (SEQ ID NO: 26), $Cys^{118}$-$Cys^{134}$-$Ala^{121}$-$Ala^{167}$-FGF-21 (SEQ ID NO: 13) in combination with $Gly^8$-$Glu^{22}$-$Gly^{36}$-GLP-1-1L-IgG4 (S228P, F234A, L235A, N297A) (SEQ ID NO: 27), $Cys^{118}$-$Cys^{134}$-$Ala^{121}$-$Ala^{167}$-FGF-21 (SEQ ID NO: 13) in combination with $Gly^8$-$Glu^{22}$-$Gly^{36}$-GLP-1-1L-IgG4 (S228P, des K) (SEQ ID NO: 28), $Cys^{118}$-$Cys^{134}$-$Ala^{121}$-$Ala^{167}$-FGF-21 (SEQ ID NO: 13) with $Gly^8$-$Glu^{22}$-$Gly^{36}$-GLP-1-1L-IgG4 (S228P, F234A, L235A, des K) (SEQ ID NO: 29), $Cys^{118}$-$Cys^{134}$-$Ala^{121}$-$Ala^{167}$-FGF-21 (SEQ ID NO: 13) in combination with $Gly^8$-$Glu^{22}$-$Gly^{36}$-GLP-1-1L-IgG4 (S228P, N297A, des K) (SEQ ID NO: 30), $Cys^{118}$-$Cys^{134}$-$Ala^{121}$-$Ala^{167}$-FGF-21 (SEQ ID NO: 13) in combination with $Gly^8$-$Glu^{22}$-$Gly^{36}$-GLP-1-1L-IgG4 (S228P, F234A, L235A, N297A, des K) (SEQ ID NO: 31), $Cys^{118}$-$Cys^{134}$-$Ala^{121}$-$Ala^{167}$-FGF-21 (SEQ ID NO:13) in combination with $Gly^8$-$Glu^{22}$-$Gly^{36}$-GLP-1-1.5L-IgG4 (S228P) (SEQ ID NO: 32), $Cys^{118}$-$Cys^{134}$-$Ala^{121}$-$Ala^{167}$-FGF-21 (SEQ ID NO: 13) in combination with $Gly^8$-$Glu^{22}$-$Gly^{36}$-GLP-1-1.5L-IgG4 (S228P, F234A, L235A) (SEQ ID NO: 33), $Cys^{118}$-$Cys^{134}$-$Ala^{121}$-$Ala^{167}$-FGF-21 (SEQ ID NO: 13) in combination with $Gly^8$-$Glu^{22}$-$Gly^{36}$-GLP-1-1.5L-IgG4 (S228P, N297A) (SEQ ID NO: 34), $Cys^{118}$-$Cys^{134}$-$Ala^{121}$-$Ala^{167}$-FGF-21 (SEQ ID NO: 13) in combination with $Gly^8$-$Glu^{22}$-$Gly^{36}$-GLP-1-1.5L-IgG4 (S228P, F234A, L235A, N297A) (SEQ ID NO: 35), $Cys^{118}$-$Cys^{134}$-$Ala^{167}$-FGF-21 (SEQ ID NO: 13) in combination with $Gly^8$-$Glu^{22}$-$Gly^{36}$-GLP-1-1.5L-IgG4 (S228P, des K) (SEQ ID NO: 36), $Cys^{118}$-$Cys^{134}$-$Ala^{121}$-$Ala^{167}$-FGF-21 (SEQ ID NO: 13) in combination with $Gly^8$-$Glu^{22}$-$Gly^{36}$-GLP-1-1.5L-IgG4 (S228P, F234A, L235A, des K) (SEQ ID NO: 37), $Cys^{118}$-$Cys^{134}$-$Ala^{121}$-$Ala^{167}$-FGF-21

(SEQ ID NO: 13) in combination with Gly$^8$-Glu$^{22}$-Gly$^{36}$-GLP-1-1.5L-IgG4 (S228P, N297A, des K) (SEQ ID NO: 38), Cys$^{118}$-Cys$^{134}$-Ala$^{121}$-Ala$^{167}$-FGF-21 (SEQ ID NO: 13) in combination with Gly$^8$-Glu$^{22}$-Gly$^{36}$-GLP-1-1.5L-IgG4 (S228P, F234A, L235A, N297A, des K) (SEQ ID NO: 39), Cys$^{118}$-Cys$^{134}$-Ala$^{121}$-Ala$^{167}$-FGF-21 (SEQ ID NO: 13) in combination with Gly$^8$-Glu$^{22}$-Gly$^{36}$-GLP-1-2L-IgG4 (S228P) (SEQ ID NO: 40), Cys$^{118}$-Cys$^{134}$-Ala$^{121}$-Ala$^{167}$-FGF-21 (SEQ ID NO: 13) in combination with Gly$^8$-Glu$^{22}$-Gly$^{36}$-GLP-1-2L-IgG4 (S228P, F234A, L235A) (SEQ ID NO: 41), Cys$^{118}$-Cys$^{134}$-Ala$^{121}$-Ala$^{167}$-FGF-21 (SEQ ID NO: 13) in combination with Gly$^8$-Glu$^{22}$-Gly$^{36}$-GLP-1-2L-IgG4 (S228P, N297A) (SEQ ID NO: 42), Cys$^{118}$-Cys$^{134}$-Ala$^{121}$-Ala$^{167}$-FGF-21 (SEQ ID NO: 13) in combination with Gly$^8$-Glu$^{22}$-Gly$^{36}$-GLP-1-2L-IgG4 (S228P, F234A, L235A, N297A) (SEQ ID NO: 43), Cys$^{118}$-Cys$^{134}$-Ala$^{121}$-Ala$^{167}$-FGF-21 (SEQ ID NO: 13) in combination with Gly$^8$-Glu$^{22}$-Gly$^{36}$-GLP-1-2L-IgG4 (S228P, des K) (SEQ ID NO: 44), Cys$^{118}$-Cys$^{134}$-Ala$^{121}$-Ala$^{167}$-FGF-21 (SEQ ID NO: 13) in combination with Gly$^8$-Glu$^{22}$-Gly$^{36}$-GLP-1-2L-IgG4 (S228P, F234A, L235A, des K) (SEQ ID NO: 45), Cys$^{118}$-Cys$^{134}$-Ala$^{121}$-Ala$^{167}$-FGF-21 (SEQ ID NO: 13) in combination with Gly$^8$-Glu$^{22}$-Gly$^{36}$-GLP-1-2L-IgG4 (S228P, N297A, des K) (SEQ ID NO: 46), Cys$^{118}$-Cys$^{134}$-Ala$^{121}$-Ala$^{167}$-FGF-21 (SEQ ID NO: 13) in combination with Gly$^8$-Glu$^{22}$-Gly$^{36}$-GLP-1-2L-IgG4 (S228P, F234A, L235A, N297A, des K) (SEQ ID NO: 47), Cys$^{118}$-Cys$^{134}$-Ala$^{121}$-Ala$^{167}$-FGF-21 (SEQ ID NO: 13) in combination with exendin-4 (SEQ ID NO: 4), Cys$^{118}$-Cys$^{134}$-Ala$^{121}$-Ala$^{167}$-FGF-21 (SEQ ID NO: 13) in combination with albiglutide (SEQ ID NO: 49), Cys$^{118}$-Cys$^{134}$-Ala$^{167}$-FGF-21 (SEQ ID NO:10) in combination with a GLP-1 compound comprising the amino acid sequence of SEQ ID NO: 47, Cys$^{118}$-Cys$^{134}$-Ala$^{167}$-FGF-21 (SEQ ID NO: 10) in combination with a GLP-1 compound consisting of the amino acid sequence of SEQ ID NO: 47, Cys$^{118}$-Cys$^{134}$-Ala$^{121}$-Ala$^{167}$-FGF-21 (SEQ ID NO: 13) in combination with a GLP-1 compound comprising the amino acid sequence of SEQ ID NO: 48, Cys$^{118}$-Cys$^{134}$-Ala$^{121}$-Ala$^{167}$-FGF-21 (SEQ ID NO: 13) in combination with a GLP-1 compound consisting of the amino acid sequence of SEQ ID NO: 48, Cys$^{118}$-Cys$^{134}$-Ala$^{121}$-Ala$^{167}$-FGF-21 (SEQ ID NO: 13) in combination with a GLP-1 compound comprising the amino acid sequence of SEQ ID NO: 49, Cys$^{118}$-Cys$^{134}$-Ala$^{121}$-Ala$^{167}$-FGF-21 SEQ ID NO: 13) in combination with a GLP-1 compound consisting of the amino acid sequence of SEQ ID NO: 49, Cys$^{118}$-Cys$^{134}$-Ala$^{121}$-Ala$^{167}$-FGF-21 (SEQ ID NO: 13) in combination with a GLP-1 compound comprising the amino acid sequence of SEQ ID NO: 50, Cys$^{118}$-Cys$^{134}$-Ala$^{121}$-Ala$^{167}$-FGF-21 (SEQ ID NO: 13) in combination with a GLP-1 compound consisting of the amino acid sequence of SEQ ID NO: 50, Cys$^{118}$-Cys$^{134}$-Ala$^{121}$-Ala$^{167}$-FGF-21 (SEQ ID NO: 13) in combination with a GLP-1 compound comprising the amino acid sequence of SEQ ID NO: 51, Cys$^{118}$-Cys$^{134}$-Ala$^{121}$-Ala$^{167}$-FGF-21 (SEQ ID NO: 13) in combination with a GLP-1 compound consisting of the amino acid sequence of SEQ ID NO: 51, Cys$^{118}$-Cys$^{134}$-Ala$^{121}$-Ala$^{167}$-FGF-21 (SEQ ID NO: 13) in combination with a GLP-1 compound comprising the amino acid sequence of SEQ ID NO: 52. Cys$^{118}$-Cys$^{134}$-Ala$^{121}$-Ala$^{167}$-FGF-21 (SEQ ID NO: 13) in combination with a GLP-1 compound consisting of the amino acid sequence of SEQ ID NO: 52, Cys$^{118}$-Cys$^{134}$-Ala$^{121}$-Ala$^{167}$-FGF-21 (SEQ ID NO: 13) in combination with a GLP-1 compound comprising the amino acid sequence of SEQ ID NO: 53, Cys$^{118}$-Cys$^{134}$-Ala$^{121}$-Ala$^{167}$-FGF-21 (SEQ ID NO: 13) in combination with a GLP-1 compound consisting of the amino acid sequence of SEQ ID NO: 53, Cys$^{118}$-Cys$^{134}$-Ala$^{121}$-Ala$^{167}$-FGF-21 (SEQ ID NO: 13) in combination with a GLP-1 compound comprising the amino acid sequence of SEQ ID NO: 54, Cys$^{118}$-Cys$^{134}$-Ala$^{121}$-Ala$^{167}$-FGF-21 (SEQ ID NO: 13) in combination with a GLP-1 compound consisting of the amino acid sequence of SEQ ID NO: 54, Cys$^{118}$-Cys$^{134}$-Ala$^{121}$-Ala$^{167}$-FGF-21 (SEQ ID NO: 13) in combination with a GLP-1 compound comprising the amino acid sequence of SEQ ID NO: 55, Cys$^{118}$-Cys$^{134}$-Ala$^{121}$-Ala$^{167}$-FGF-21 (SEQ ID NO: 13) in combination with a GLP-1 compound consisting of the amino acid sequence of SEQ ID NO: 55, Cys$^{118}$-Cys$^{134}$-Ala$^{121}$-Ala$^{167}$-FGF-21 (SEQ ID NO: 13) in combination with a GLP-1 compound comprising the amino acid sequence of SEQ ID NO: 56, Cys$^{118}$-Cys$^{134}$-Ala$^{121}$-Ala$^{167}$-FGF-21 (SEQ ID NO: 13) in combination with a GLP-1 compound consisting of the amino acid sequence of SEQ ID NO: 56, Cys$^{118}$-Cys$^{134}$-Ala$^{121}$-Ala$^{167}$-FGF-21 (SEQ ID NO: 13) in combination with a GLP-1 compound comprising the amino acid sequence of SEQ ID NO: 57, and Cys$^{118}$-Cys$^{134}$-Ala$^{121}$-Ala$^{167}$-FGF-21 (SEQ ID NO: 13) in combination with a GLP-1 compound consisting of the amino acid sequence of SEQ ID NO: 57.

In a preferred embodiment, the combination of the present invention comprises an FGF-21 analog comprising the amino acid sequence of Cys$^{118}$-Cys$^{134}$-Ala$^{121}$-Ala$^{167}$-FGF-21 (SEQ ID NO: 13) in combination with a GLP-1 analog, wherein the GLP-1 analog comprises the amino acid sequence of Val$^8$-Glu$^{22}$-GLP-1 (SEQ ID NO: 17) with five additional amino acid sequence substitutions. In a preferred embodiment, the combination of the present invention comprises an FGF-21 analog consisting of the amino acid sequence of Cys$^{118}$-Cys$^{134}$-Ala$^{121}$-Ala$^{167}$-FGF-21 (SEQ ID NO: 13) in combination with a GLP-1 analog, wherein the GLP-1 analog consists of the amino acid sequence of Val$^8$-Glu$^{22}$-GLP-1 (SEQ ID NO: 17) with five additional amino acid sequence substitutions. In another preferred embodiment, the combination of the present invention comprises an FGF-21 analog comprising the amino acid sequence of Cys$^{118}$-Cys$^{134}$-Ala$^{121}$-Ala$^{167}$-FGF-21 (SEQ ID NO: 13) in combination with a GLP-1 analog, wherein the GLP-1 analog comprises the amino acid sequence of Val$^8$-Glu$^{22}$-GLP-1 (SEQ ID NO: 17) with four additional amino acid sequence substitutions. In another preferred embodiment, the combination of the present invention comprises an FGF-21 analog consisting of the amino acid sequence of Cys$^{118}$-Cys$^{134}$-Ala$^{121}$-Ala$^{167}$-FGF-21 (SEQ ID NO: 13) in combination with a GLP-1 analog, wherein the GLP-1 analog consists of the amino acid sequence of Val$^8$-Glu$^{22}$-GLP-1 (SEQ ID NO: 17) with four additional amino acid sequence substitutions. In another preferred embodiment, the combination of the present invention comprises an FGF-21 analog comprising the amino acid sequence of Cys$^{118}$-Cys$^{134}$-Ala$^{121}$-Ala$^{167}$-FGF-21 (SEQ ID NO: 13) in combination with a GLP-1 analog, wherein the GLP-1 analog comprises the amino acid sequence of Val$^8$-Glu$^{22}$-GLP-1 (SEQ ID NO: 17) with three additional amino acid sequence substitutions. In another preferred embodiment, the combination of the present invention comprises an FGF-21 analog consisting of the amino acid sequence of Cys$^{118}$-Cys$^{134}$-Ala$^{121}$-Ala$^{167}$-FGF-21 (SEQ ID NO: 13) in combination with a GLP-1 analog, wherein the GLP-1 analog consists of the amino acid sequence of Val$^8$-Glu$^{22}$-GLP-1 (SEQ ID NO: 17) with three additional amino acid substitutions. In another preferred embodiment, the combination of the present invention comprises an FGF-21 analog comprising the amino acid sequence of Cys$^{118}$-Cys$^{134}$-Ala$^{121}$-Ala$^{167}$-FGF-21 (SEQ ID NO: 13) in combination with a GLP-1 analog, wherein the GLP-1 analog comprises the amino acid sequence of Val$^8$-Glu$^{22}$-GLP-1 (SEQ ID NO: 17) with two additional amino acid sequence substitutions. In another preferred embodiment, the combination of the present invention comprises an FGF-21 analog consisting of the amino acid sequence of Cys$^{118}$-Cys$^{134}$-Ala$^{121}$-Ala$^{167}$-FGF-21 (SEQ ID NO: 13) in combination with a GLP-1 analog, wherein the GLP-1 analog consists of the amino acid sequence of Val$^8$-Glu$^{22}$-GLP-1 (SEQ ID NO: 17) with two additional amino acid sequence substitutions. In another preferred embodiment, the combination of the present invention comprises an FGF-21 analog comprising the amino acid sequence of Cys$^{118}$-Cys$^{134}$-Ala$^{121}$-Ala$^{167}$-FGF-21 (SEQ ID NO: 13) in combination with a GLP-1 analog, wherein the GLP-1 analog comprises the amino acid sequence of Val$^8$-Glu$^{22}$-GLP-1 (SEQ ID NO: 17) comprises one additional amino acid sequence substitution. In another preferred embodiment, the combination of the present invention comprises an FGF-21 analog consisting of the amino acid sequence of Cys$^{118}$-Cys$^{134}$-Ala$^{121}$-Ala$^{167}$-FGF-21 (SEQ ID NO: 13) in combination with a GLP-1 analog, wherein the GLP-1 analog consists of the amino acid sequence of Val$^8$-Glu$^{22}$-GLP-1 (SEQ ID NO: 17) comprises one additional amino acid sequence substitution.

EXAMPLE 1

Effect of Combination Treatment with GLP-1 and FGF-21 on Body Weight and on Blood Glucose Levels Diet-induced obese (DIO) male C57/B16 mice (Harlan: Virginia) maintained on a calorie rich diet (TD95217, Teklad, Madison, Wis.) since weaning are used. DIO is established by ad libitum feeding for at least 7 weeks of a diet consisting of 40% fat, 39% carbohydrate, and 21% protein caloric content (TD95217). Animals are individually housed in a temperature-controlled (24° C.) facility with 12 hour light/dark cycle (lights on 2200) and free access to food (TD95217) and water. After a minimum of 2 weeks acclimation to the facility, the mice are randomized according to their body weight, so each experimental group of animals would have similar body weight.

Body composition of DIO male C57/B16 mice is determined by using QNMR analysis 1 day prior to initiation of treatment. Combination treatment is administered with two delivery methods. A FGF-21 compound (1 mg/kg) is subcutaneously injected once a day and a GLP-1 compound (3 nmol/kg/day) is delivered by continuous subcutaneous infusion with alzet pump. The experimental groups are as follow: One group ("Vehicle") of mice (n=8) receives PBS (11.4 μL/day) and a daily subcutaneous injection of 0.05 mL/10 g of PBS. Another group ("FGF-21") of mice (n=8) receives 11.4 μL/day of PBS using the alzet pump and a daily subcutaneous injection of 1 mg/kg of FGF-21. The "GLP-1" group of mice receives 3 nmol/kg/day of a GLP-1 compound through an alzet pump and a daily subcutaneous injection of 0.05 mL/10 g of PBS. The "GLP-1+FGF-21" group of mice receives 3 nmol/kg/day of a GLP-1 compound through an alzet pump and a daily subcutaneous injection of 1 mg/kg of a FGF-21 compound. Injections occur prior to the onset of the dark photoperiod. Starting weight values are measured after implantation of alzet pumps on Day 1. Body weights are recorded in conjunction with daily dosing. Average weight changes compared to starting weights of a particular treatment group, including vehicle, are determined. Average daily weight changes are normalized to average of daily weight change of Vehicle group and are reported in Table 1 (i.e., (Average weight change of Treatment group)−(Average weight change of Vehicle group)). For all treatment groups n=8.

Data in Table 1 represent results where the FGF-21 compound is human FGF-21 (SEQ ID NO: 1) and where the GLP-1 compound is Val$^8$-Glu$^{22}$-Ile$^{33}$-Gly$^{36}$-Pro$^{37}$-Ser$^{38}$-Ser$^{39}$-Gly$^{40}$-Ala$^{41}$-Pro$^{42}$-Pro$^{43}$-Pro$^{44}$-Ser$^{45}$-GLP-1 (SEQ ID NO: 19). The data demonstrate that the use of a FGF-21 compound in combination with a GLP-1 compound results in a synergistic effect on weight loss.

TABLE 1

Average Weight Change Normalized to Vehicle Treated Mice

| Treatment Day | FGF-21 (g) | GLP-1 (g) | GLP-1 + FGF-21 (g) |
|---|---|---|---|
| Day 1 | 0 | 0 | 0 |
| Day 5 | −0.45 | −1.01 | −2.62 |
| Day 10 | −1.94 | −1.99 | −5.16 |
| Day 15 | −2.85 | −2.50 | −6.94 |

We claim:

1. A method of treating diabetes comprising administering an FGF-21 compound in combination with a GLP-1 compound, wherein the FGF-21 compound has the amino acid sequence of SEQ ID NO: 2, and wherein the GLP-1 compound has the amino acid sequence of SEQ ID NO: 19.

2. A method of lowering blood glucose levels comprising administering an FGF-21 compound in combination with a GLP-1 compound, wherein the FGF-21 compound has the amino acid sequence of SEQ ID NO: 2, and wherein the GLP-1 compound has the amino acid sequence of SEQ ID NO: 19.

* * * * *